US012005260B2

(12) United States Patent
Debarros et al.

(10) Patent No.: US 12,005,260 B2
(45) Date of Patent: Jun. 11, 2024

(54) EMULATION OF ELECTROPHYSIOLOGICAL SIGNALS DERIVED BY STIMULATION OF A BODY

(71) Applicant: Oxford University Innovation Limited, Oxford (GB)

(72) Inventors: Jean Debarros, Oxford (GB); Peter Brown, Oxford (GB); Huiling Tan, Oxford (GB); Timothy Denison, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 487 days.

(21) Appl. No.: 17/429,388

(22) PCT Filed: Feb. 13, 2020

(86) PCT No.: PCT/GB2020/050337
§ 371 (c)(1),
(2) Date: Aug. 9, 2021

(87) PCT Pub. No.: WO2020/165591
PCT Pub. Date: Aug. 20, 2020

(65) Prior Publication Data
US 2022/0143415 A1 May 12, 2022

(30) Foreign Application Priority Data
Feb. 13, 2019 (GB) .................................... 1901982

(51) Int. Cl.
*A61N 1/37* (2006.01)
*A61N 1/372* (2006.01)
(52) U.S. Cl.
CPC .............................. *A61N 1/37241* (2013.01)

(58) Field of Classification Search
None
See application file for complete search history.

(56) References Cited

U.S. PATENT DOCUMENTS

2004/0139040 A1\* 7/2004 Nervegna ............... G06N 3/063
703/11
2012/0116741 A1 5/2012 Choi et al.
(Continued)

FOREIGN PATENT DOCUMENTS

WO 2018/035067 A1 2/2018

OTHER PUBLICATIONS

International Search Report and Written Opinion for WO 2020/165591 (PCT/GB2020/050337), dated May 25, 2020, pp. 1-13.
(Continued)

*Primary Examiner* — Ankit D Tejani
(74) *Attorney, Agent, or Firm* — Thomas|Horstemeyer, LLP

(57) ABSTRACT

An emulation apparatus emulates an electrophysiological signal derived from a target area of a human or animal nervous system under the influence of a stimulation signal applied to the human or animal body. A prior signal generator generates a prior signal representing an electrophysiological signal in the absence of stimulation. A test signal representing a stimulation signal is received and used by a modelling unit to derive a modulation signal representing the degree of modulation of the electrophysiological signal, in accordance with a model of the temporal evolution of the modulation of the electrophysiological signal caused by the stimulation signal. A modulation unit modulates the prior signal in accordance with the modulation signal to output an emulation signal representing an electrophysiological signal derived under the influence of the stimulation signal. The (Continued)

emulation apparatus has wide use in neuroscience research, bioengineering and clinical applications.

29 Claims, 22 Drawing Sheets

(56) References Cited

U.S. PATENT DOCUMENTS

| | | | |
|---|---|---|---|
| 2015/0246232 | A1 | 9/2015 | Kameneva et al. |
| 2017/0291031 | A1 | 10/2017 | Lee |
| 2018/0199892 | A1* | 7/2018 | Fiveland ............ A61B 5/055 |
| 2018/0199895 | A1 | 7/2018 | Fiveland et al. |

OTHER PUBLICATIONS

UK Search Report for GB 1901982.7, dated Jul. 11, 2019, pp. 1-3.
Tinkhauser, G., Pogosyan, A., Little, S., Beudel, M., Herz, D. M., Tan, H., & Brown, P., (2017), « The modulatory effect of adaptive deep brain stimulation on beta bursts in parkinson's disease », Brain, vol. 140, No. 4, p. 1053-1067, Web: https://academic.oup.com/brain/article/140/4/1053/2993763.
Wills, A., Schon, T. B., Ljung, L., & Ninness, B., (2013), « Identification of hammerstein-wiener models », Automatica, vol. 49, No. 1, p. 70-81, Web: http://www.sciencedirect.com/science/article/pii/S0005109812004815.
Qian, X., Chen, Y., Feng, Y., Ma, B., Hao, H., & Li, L., (2017), « A method for removal of deep brain stimulation artifact from local field potentials », IEEE transactions on neural systems and rehabilitation engineering: a publication of the IEEE Engineering in Medicine and Biology Society, vol. 25, No. 12, p. 2217-2226.
Koss, A. M., Alterman, R. L., Tagliati, M., & Shils, J. L., (2005), « Calculating total electrical energy delivered by deep brain stimulation systems », Annals of Neurology, vol. 58, No. 1, p. 168-168, Web: http://doi.wiley.com/10.1002/ana.20525.
Hutcheon, B. & Yarom, Y., (2000), « Resonance, oscillation and the intrinsic frequency preferences of neurons », Trends in Neurosciences, vol. 23, No. 5, p. 216-222, Web: http://linkinghub.elsevier.com/retrieve/pii/S0166223600015472.
Grossman, N., Bono, D., Dedic, N., Kodandaramaiah, S. B., Rudenko, A., Suk, H.-J., . . . Boyden, E. S., (2017), « Noninvasive deep brain stimulation via temporally interfering electric fields », Cell, vol. 169, No. 6, p. 1029-1041.e16, Web: https://linkinghub.elsevier.com/retrieve/pii/S0092867417305846.
Birdno, M. J. & Grill, W. M., (2008), « Mechanisms of deep brain stimulation in movement disorders as revealed by changes in stimulus frequency », Neurotherapeutics, vol. 5, No. 1, p. 14-25.
Van Albada, S. J. & Robinson, P. A., (2009), « Mean-field modeling of the basal ganglia-thalamocortical system. i », Journal of Theoretical Biology, vol. 257, No. 4, p. 642-663, Jan. 8, 2018 Web: http://linkinghub.elsevier.com/retrieve/bii/S0022519308006486.
Van Albada, S. J., Gray, R. T., Drysdale, P. M., & Robinson, P. A., (2009), « Mean-field modeling of the basal ganglia-thalamocortical system. ii », Journal of Theoretical Biology, vol. 257, No. 4, p. 664-688, Web: http://linkinghub.elsevier.com/retrieve/pii/S0022519308006474.

Grado, L. L., Johnson, M. D., & Netoff, T. I., (2018), « Bayesian adaptive dual control of deep brain stimulation in a computational model of parkinson's disease », PLOS Computational Biology, vol. 14, No. 12, p. e1006606, Web: https://journals.plos.org/ploscompbiol/article?id=10.1371/journal.pcbi.1006606.
Sooksood, K., Stieglitz, T., & Ortmanns, M., (2010), « An active approach for charge balancing in functional electrical stimulation », IEEE Transactions on Biomedical Circuits and Systems, vol. 4, No. 3, p. 162 170.
Little, S., Pogosyan, A., Neal, S., Zavala, B., Zrinzo, L., Hariz, M., . . . Brown, P., (2013), 'Adaptive deep brain stimulation in advanced parkinson disease: adaptive dbs in pd', Annals of Neurology, vol. 74, No. 3, pp. 449-457, Web: http://doi.wiley.com/10.1002/ana.23951.
Basu, I., Robertson, M. M., Crocker, B., Peled, N., Farnes, K., Vallejo-Lopez, D. I., . . . Cash, S. S., (2019), « Consistent linear and non-linear responses to invasive electrical brain stimulation across individuals and primate species with implanted electrodes », Brain Stimulation, vol. 12, No. 4, p. 877 892, Web: https://linkinghub.elsevier.com/retrieve/pii/S1935861X19300865.
Bouthour, W., Wegrzyk, J., Momjian, S., Peron, J., Fleury, V., Chaoui, E. T., . . . Zacharia, A., (2018), « Short pulse width in subthalamic stimulation in parkinson's disease: a randomized, double-blind study », Movement Disorders, vol. 33, No. 1, p. 169 173, Web: https://onlinelibrary.wiley.com/doi/abs/10.1002/mds.27265.
Haddock, A., Mitchell, K. T., Miller, A., Ostrem, J. L., Chizeck, H. J., & Miocinovic, S., (2018), « Automated deep brain stimulation programming for tremor », IEEE Transactions on Neural Systems and Rehabilitation Engineering, p. 1 1, Web: https://ieeexplore.ieee.org/document/8401333.
Lempka, S. F., Howell, B., Gunalan, K., Machado, A. G., & McIntyre, C. C., (2018), « Characterization of the stimulus waveforms generated by implantable pulse generators for deep brain stimulation », Clinical Neurophysiology, vol. 129, No. 4, p. 731 742, Web: http://www.sciencedirect.com/science/article/pii/S1388245718300300.
Neumann, W.-J., Memarian Sorkhabi, M., Benjaber, M., Feldmann, L. K., Saryyeva, A., Krauss, J. K., . . . Denison, T., (2021), « The sensitivity of ecg contamination to surgical implantation site in brain computer interfaces », Brain Stimulation, vol. 14, No. 5, p. 1301 1306, Web: https://www.sciencedirect.com/science/article/pii/S1935861X21002187.
Steigerwald, F., Timmermann, L., Kühn, A., Schnitzler, A., Reich, M. M., Kirsch, A. D., . . . Volkmann, J., (2018), « Pulse duration settings in subthalamic stimulation for parkinson's disease », Movement Disorders, vol. 33, No. 1, p. 165 169, Web: https://onlinelibrary.wiley.com/doi/abs/10.1002/mds.27238.
Wiest, C., Tinkhauser, G., Pogosyan, A., Bange, M., Muthuraman, M., Groppa, S., . . . Torrecillos, F., (2020), « Local field potential activity dynamics in response to deep brain stimulation of the subthalamic nucleus in parkinson's disease », Neurobiology of Disease, vol. 143, p. 105019, Web: https://linkinghub.elsevier.com/retrieve/pii/S0969996120302941.
International Preliminary Report on Patentability for WO 2020/165591 (PCT/GB2020/050337), dated Aug. 10, 2021, pp. 1-7.

* cited by examiner

EMULATION OF ELECTROPHYSIOLOGICAL SIGNALS DERIVED BY STIMULATION OF A BODY

CROSS-REFERENCE TO RELATED APPLICATIONS

This application is the National Stage of International Application No. PCT/GB2020/050337, filed Feb. 13, 2020, which claims priority to GB 1901982.7, filed Feb. 13, 2019, which are entirely incorporated herein by reference.

The present invention relates to electrophysiological signals derived from a target area of the nervous system of a human or animal body under the influence of stimulation signals applied to the human or animal body.

Electrophysiological signals derived from a target area of the nervous system of a human or animal body are known to provide information about neurological function. It is also known that the electrophysiological signals may be influenced by stimulation signals applied to the human or animal body. This effect can be used to treat neurological disorders.

By way of example, Deep Brain Stimulation (DBS) is a standard treatment for a variety of movement disorders such as Parkinson's Disease, Dystonia and Essential Tremor. DBS has been also proposed and tested for the treatment of psychiatric disorders such as major depression, obsessive compulsive disorder (OCD), addiction and eating disorders. Conventional DBS delivers continuous stimulation at a fixed high frequency stimulation and constant amplitude. Adaptive deep brain stimulation (aDBS) aims to improve efficacy, efficiency and selectivity of the treatment by using dynamic markers of disease activity to optimise and control DBS. One particularly informative biomarker for Parkinson's disease is oscillatory activity in the beta frequency band (~20 Hz) in the local field potential (LFP) recorded directly from the stimulation electrode when the latter is implanted in the subthalamic nucleus (STN) or globus pallidus interna (GPi).

Currently existing DBS system delivers constant stimulation to the brain at a level set by a medical staff. A closed-loop DBS system may be used to automatically adjust the parameters of the stimulation signal in real-time based on the brain response to the electrical stimulation, and therefore offers a great potential to further improve efficacy, reduce side effects and decrease treatment cost. However, closed-loop DBS control requires a good understanding of the dynamic response of the LFP signal to the stimulation [Reference 1].

Other scenarios where such closed-loop stimulation may be performed include (but are not limited to), closed-loop spinal cord stimulation, peripheral or autonomic nerve stimulation, and closed-loop non-invasive brain stimulation.

Such stimulation treatment confers major therapeutic benefits and are life-changing for many conditions, so there is a need for development of stimulation systems and protocols for their use.

The difficulty and often infeasibility in testing different control algorithms in real patients is a main obstacle in the research for improving the algorithms for close-loop stimulation. Meanwhile, lack of understanding on how the stimulator will behave given the variations in the electrophysiological signals in patients during the closed-loop stimulation protocol reduces the confidence of the clinical team in implementing those more advanced protocols, compared to the traditional stimulation protocol, in which all the stimulation parameters are under the manual control of the clinical carer.

According to a first aspect of the present invention, there is provided an emulation apparatus arranged to emulate an electrophysiological signal derived from a target area of the nervous system of a human or animal body under the influence of a stimulation signal applied to the human or animal body, the emulation apparatus comprising: a prior signal generator arranged to generate a prior signal representing an electrophysiological signal derived from a target area of the nervous system of a human or animal body in the absence of a stimulation signal; a test signal input arranged to receive a test signal representing a stimulation signal applied to the human or animal body; a modelling unit arranged to derive a modulation signal, which modulation signal represents the degree of modulation of the electrophysiological signal by the stimulation signal, from the test signal in accordance with a model implemented within the modelling unit of the temporal evolution of the modulation of the electrophysiological signal caused by the stimulation signal; and a modulation unit arranged to modulate the prior signal in accordance with the modulation signal to output an emulation signal representing an electrophysiological signal derived under the influence of the stimulation signal.

The emulation apparatus is therefore a tool that provides emulation of an electrophysiological signal derived from a target area of the nervous system of a human or animal body under the influence of a stimulation signal applied to the human or animal body, and is a core part of the intelligent deep brain stimulation system (iDBS) for advanced control of the nervous system. This is achieved based on an appreciation that the temporal evolution of the modulation of the electrophysiological signal caused by the stimulation signal may be modelled. Such a model may take advantage of knowledge about the physiological response of the specific target area to electrical stimulation. Accordingly, a model of that temporal evolution is implemented with a modelling unit and is used to derive a modulation signal which represents the degree of modulation of the electrophysiological signal. The modulation signal is used to modulate a prior signal representing the electrophysiological signal, and thereby to output an emulation signal representing an electrophysiological signal derived under the influence of the stimulation signal.

This allows the effect of stimulation signals represented by the test signal to be understood, which is useful in a wide range of applications, some examples of which are as follows.

One type of application is the study of stimulation by neuroscience researchers, the development of stimulation systems by bioengineers, and the training of clinicians.

The emulation apparatus allows researchers to explore complex control algorithms capable to adapt automatically to a specific patient, and simultaneously addressing multiple symptoms. The emulation apparatus similarly allows testing in real-time of the developed algorithms, the research protocol and safety of their experiments before collecting data from patients. This provides optimal use of scarce recording opportunities and high-quality data from experiments. The emulation apparatus can be extended to any medical condition where a set of signals respond to electrical stimulation by updating the structure of the model and its implementation.

Bioengineers developing stimulation systems are provided with the same benefits as researchers. At the present time, control algorithms embedded in implanted medical devices are simple, but the design of more complex control algorithms for the stimulation signal requires the possibility to test both functionality and real-time electrical behaviours for improving reliability and safety prior to clinical use. In addition, the emulation apparatus can provide evidence to demonstrate to regulatory bodies that equipment has been thoroughly tested for scenarios not easily reproducible with animal testing or with human for ethical reasons, based on a proved mathematical model. This approach is known to facilitate significantly regulatory approval.

Another type of application is to assist clinicians with clinical usage of stimulation systems. The emulation apparatus may assist clinicians with training, for example by facilitating a clinician to train on a specific stimulation system in an environment very much like that of a patient. The emulation apparatus may also assist clinicians with clinical usage of a stimulation system to treat a condition of a specific patient. For example, templates of specific disease conditions and/or information from the patient allows the clinician to carry out tests of their clinical interventions ahead of time and to derive a suitable parameters for the stimulation signal. This can improve both the patient's safety and the clinician's efficiency. Therefore, the emulation apparatus presented here is a core part of the intelligent deep brain stimulation system (iDBS) for advanced control of neurological medical conditions.

The stimulation signal may be a DBS stimulation signal for application to a target area of the brain of the human or animal body in DBS, for example aDBS. However, the techniques disclosed herein is equally applicable to other forms of stimulation of any part of the nervous system of a human or animal body.

For example, the techniques described herein may be applied to neuroscience applications where the stimulation signal target area is in the brain or any other part of the nervous system. A few examples are: closed-loop deep-brain stimulation for movement disorders or psychiatric disorders, closed-loop spinal cord stimulation (as used for example in chronic pain management), closed-loop cortical stimulation (as used for example in seizure control), peripheral or autonomic nerve stimulation, or closed-loop non-invasive brain stimulation.

Preferably, the model may include some or all of the following features.

The model may represent an algebraic change in the modulation with at least one parameter of the stimulation signal. The algebraic change may be for example an algebraic decrease, which may be an exponential decrease.

The model may include at least one differential stage, preferably two cascaded differential stages with time constants of different orders of magnitude. The differential stages may be, for example, of first order. One of the time constants may correspond to the low pass response of neural membranes of neurons to the stimulation signal. One of the time constants may represents the dynamic response of a gross average of the electrophysiological signal derived from the target area of the nervous system to the stimulation signal.

The model may further represent a saturation of the modulation at a magnitude that is dependent on at least one parameter of the stimulation signal, preferably being dependent on plural parameters of the stimulation signal.

The model may represent a gain of the modulation with respect to plural parameters of the stimulation signal.

Optionally, the emulation apparatus may further comprise an external disturbance signal generator arranged to generate an external disturbance signal representing external disturbances to the electrophysiological signal, the modulation unit being arranged to add the external disturbance signal to the emulation signal. For example, the external disturbances may include one or more of: artefacts of the stimulation signal on the signal measured from the human or animal body; DC-drift bias; electrocardiogram artefacts; and electrical noise. This is not essential and relates to practical considerations rather the target area itself. However, the use of the external disturbance signal is useful because it advantageously produces a modulation signal that more closely represents the electrophysiological signal that is derived under the influence of the stimulation signal in a practical system.

The prior signal may be, or may be derived from, a signal measured from an actual human or animal body. This allows the emulation apparatus to provide information based on actual human or animal data. This is useful in many applications, for example where a clinician is deriving suitable parameters for a stimulation signal to treat a specific patient.

Alternatively, the prior signal may be a synthetic signal. This is useful in many applications, for example allowing testing of stimulation signals over a wider range of patient parameters for which measured data is not available, for example due to scarcity of data or to cover situations for which it would be dangerous or unethical to take measurements.

The electrophysiological signal represented by the prior signal may be a signal representing a frequency domain parameter of a signal measured from the human or animal body in the absence of a stimulation signal. The measured signal may be a measured voltage, for example an LFP signal in the case of DBS. Similarly, the signal representing a frequency domain parameter thereof may be the power of given frequency band, for example a beta band signal in the case of DBS.

As an alternative, the electrophysiological signal represented by the prior signal could be an actual signal measured from the human or animal body, for example a measured voltage such as an LFP signal in the case of DBS. In that case, the emulation apparatus may further comprise a frequency domain processing unit arranged to process the emulation signal in the frequency domain to derive a processed emulation signal representing a frequency domain parameter of the electrophysiological signal derived under the influence of the stimulation signal, for example a beta band signal in the case of DBS.

The test signal may comprise a temporal signal representing the stimulation signal or may comprise parameters representing the waveform of the stimulation signal.

The emulation apparatus may be implemented in hardware by electronic components, may be implemented in software by a computer program, or a combination of both.

According to a second aspect of the present invention, there is provided a method similar to that implemented in the emulation apparatus.

The steps of the method may be performed by a computer apparatus. Thus, further according to the second aspect of the present invention, there may be provided a computer program capable of execution by a computer apparatus and configured, on execution, to cause the computer apparatus to perform the method according to the second aspect of the present invention. The computer program may be stored on a computer-readable storage medium.

To allow better understanding, an embodiment of the present invention will now be described by way of non-limitative example with reference to the accompanying drawings, in which.

Figure 1:
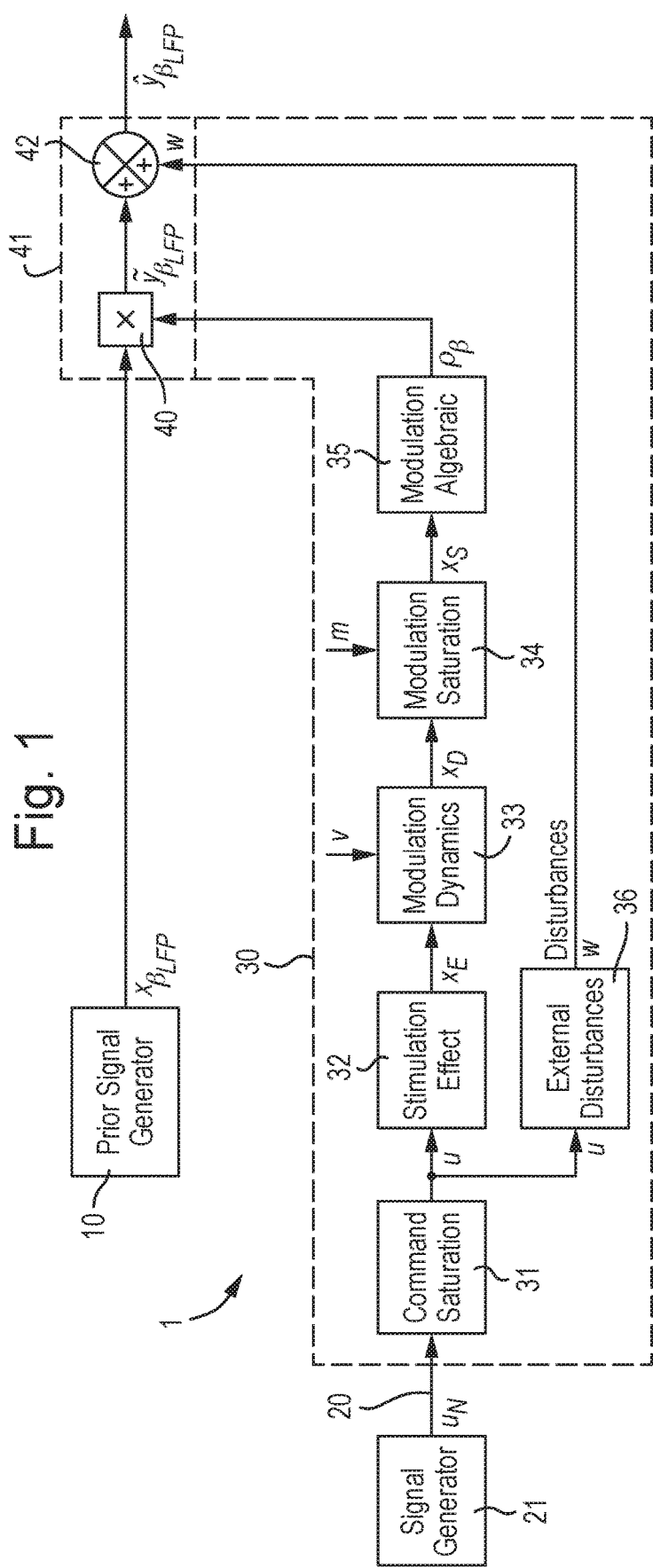
FIG. 1 is a functional block diagram of an emulation apparatus.

FIG. 1 illustrates an emulation apparatus 1 that emulates an electrophysiological signal derived from a target area of the nervous system of a human or animal body under the influence of a stimulation signal applied to the human or animal body, i.e. an externally generated electrical signal. The application to the human or animal body may in general be by any appropriate means, for example by an electrode in the example of DBS described below, or by other types of probe such as a coil.

As described further below, the emulation apparatus 1 may be implemented in hardware or software, but in both cases the emulation apparatus 1 receives a test signal representing a stimulation signal applied to the human or animal body and outputs an emulation signal representing an electrophysiological signal derived under the influence of the stimulation signal represented by the test signal. The emulation apparatus 1 is capable of closely reproducing the electrical, temporal and spectral behaviour of electrophysiological signals seen in patients. The electrophysiological signal represented by the output emulation signal may be studied as a response to different stimulation signals represented by the test signal.

As such the emulation apparatus 1 provides a practical tool for neuroscience researchers and bioengineers as described above, for example for designing, developing and testing advanced control algorithms prior to clinical tests and chronic implementation in patients.

The example of the emulation apparatus 1 described in detail below relates specifically to DBS, in which the target area is the subthalamic nucleus (STN) or globus pallidus interna (GPi), and the electrophysiological signal is a beta band signal which is a frequency domain parameter in the beta frequency band (~20 Hz) derived from the LFP signal by frequency domain processing. Similarly, the stimulation signal has a waveform for deep brain stimulation of the brain. The waveform may be selected to treat a disorder in the brain, including movement disorders, such as Parkinson's disease (PD), or other neurological and psychiatric disorders. The stimulation signal may take a conventional form for this purpose.

Figure 2:
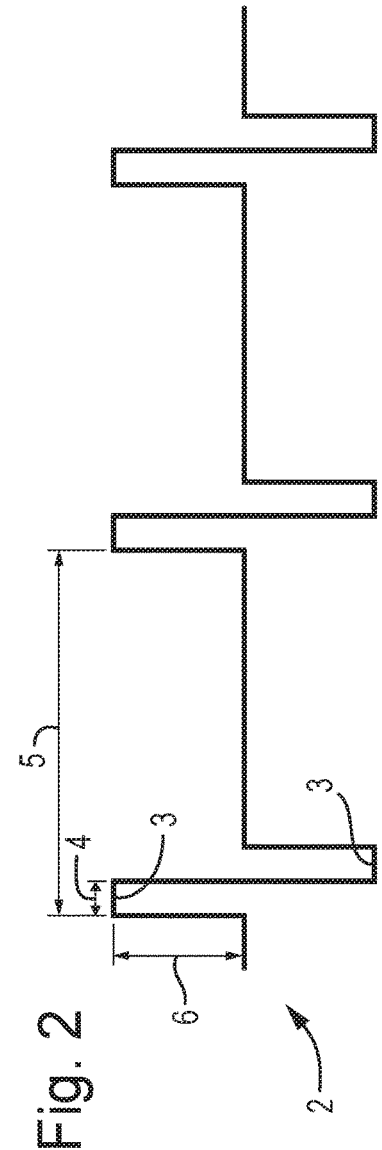
FIG. 2 is a schematic diagram of the waveform of a stimulation signal for DBS.

By way of example, the stimulation signal may have a waveform 2 as shown in FIG. 2. In this example, the stimulation signal comprises a pair of stimulation pulses 3 of positive and negative polarity. The stimulation pulses 3 are square in the example of FIG. 2 but in general may be of other shapes. The stimulation pulses 3 may have widths 4 in a range from a lower limit of 0.1 µs, preferably 1 µs, to an upper limit of 5000 ms, preferably 500 µs. For example, the width 4 may typically be 60 µs. The stimulation pulses 3 may have widths 4 that are the same or different. The pairs of stimulation pulses 3 may have no separation or may have a separation. Where present, the separation may be less than 1000 µs, preferably less than 500 µs, typically 20 µs, and/or may be less than the duration of each of the pulses. The stimulation pulses may have an amplitude 5 in a range from 0.1 V to 10.0 V. The stimulation signal may have a period 6 corresponding to a stimulation frequency in the range from 1 Hz to 500 Hz, typically being 130 Hz in currently available devices.

However, the example of DBS is not limitative, and the emulation apparatus 1 may be adapted to other forms of stimulation of any target area of the nervous system of a human or animal body. For example, the emulation apparatus 1 may be applied to neuroscience applications where the target area is in the brain or any other part of the nervous system. As mentioned above, a few examples are: closed-loop deep-brain stimulation for movement disorders or psychiatric disorders, closed-loop spinal cord stimulation (as used for example in chronic pain management), closed-loop cortical stimulation (as used for example in seizure control), peripheral or autonomic nerve stimulation, or closed-loop non-invasive brain stimulation.

Similarly, the electrophysiological signal derived from a target area of the nervous system of a human or animal body may be of any form without limitation to the example of a beta band signal. Some non-limitative alternative examples are an EMG (electromyogram) signal, and EEG (electroencephalogram) signal, a MEG (magnetoencephalography) signal or a ECG (Electrocardiogram) signal. The electrophysiological signal may be of any electrical type including a voltage physiological signal, a current physiological signal, an electrode impedance signal, and may in general be an analogue signal or a digital signal.

The emulation apparatus 1 will now be described in more detail. The emulation apparatus 1 implements a model of the target area in order to emulate the electrophysiological system. The emulation apparatus 1 includes various functional blocks that implement the model. Thus, the functional blocks in operation perform steps of a method of emulating an electrophysiological signal derived from a target area of the nervous system of a human or animal body under the influence of a stimulation signal applied to the human or animal body.

To assist understanding in view of the complexity, the functions of the functional blocks will be described first, before then describing the software and hardware implementations of those functional blocks within the emulation apparatus 1.

The emulation apparatus 1 includes a prior signal generator 10 that generates a prior signal representing the beta band signal, which is the electrophysiological signal in this case, derived from the target area in the absence of the stimulation signal.

The prior signal may be a signal that is, or is derived from, a signal measured from an actual human or animal body. For example, the signal may be measured from an actual patient to be treated by a stimulation signal.

Alternatively, the prior signal may be a synthetic signal. In this case, the prior signal generator 10 may implement a simplified and hypothetical representation how beta activity is generated at the neural network level by a generator with different degrees of a tonic activity corresponding to ongoing relatively stable background beta activity, and a phasic activity representing a more sporadic bursting activity to produce the beta band signal extracted from the overall local field potential recorded from the implanted electrodes.

In either case, the beta band signal can be either expressed in the power domain by $$x_{\beta_{LFP}(dB)},$$

or in the voltage domain by $$x_{\beta_{LFP}(V)}$$

(as described below in more detail).

The emulation apparatus 1 has a test signal input 20 that receives a test signal $u_N$ representing a stimulation signal applied to the human or animal body.

The test signal may comprise a temporal signal representing the stimulation signal, for example being a temporal signal having the waveform 2 of the stimulation signal shown in FIG. 2. The test signal $u_N$ may be generated by a test signal generator 21.

Alternatively, the test signal may comprise parameters representing the waveform of the stimulation signal. For example in the case of the waveform 2 of the stimulation signal shown in FIG. 2, the parameters may be the amplitude $u_{Na}$, pulse-width $u_{Np}$ and frequency $u_{Nf}$ of the stimulation signal.

The emulation apparatus 1 includes a modelling unit 30 which derives a modulation signal that represents the degree of modulation $\rho_\beta$ of the beta band signal by the stimulation signal. The emulation apparatus 1 is based on an appreciation that the stimulation signal modulates the beta band signal and that is possible to model the temporal evolution of the modulation from the stimulation signal. Accordingly, the modelling unit 30 derives the modulation signal from the test signal which represents the stimulation signal in accordance with a model implemented within the modelling unit 30 described in detail below.

Thus, the emulation apparatus 1 also includes a modulation unit 40 that modulates the prior signal in accordance with the modulation signal. As the prior signal represents the beta band signal derived from the target area in the absence of the stimulation signal and the modulation signal represents the degree of modulation caused by the stimulation signal, the modulation unit 40 outputs an emulation signal $\hat{y}_{\beta_{LFP}}$ that represents the beta band signal derived under the influence of the stimulation signal. This may be implemented by the modulation unit 40 including a multiplier 41 (in software or hardware) that multiplies the prior signal representing the beta band signal $x_{\beta_{LFP}}$ by the modulation signal $\rho_\beta$ representing the degree of modulation, both being temporal signals, thereby producing the emulation signal $\hat{y}_{\beta_{LFP}}$ representing the beta band signal derived under the influence of the stimulation signal.

The modelling unit 30 implements the model of the temporal evolution of the modulation of the beta band signal caused by the stimulation signal models based on a Hammerstein-Wiener model structure [Reference 2]. In particular, the modelling unit 30 includes functional blocks which operate on the test signal. An overview of the functional blocks of the modelling unit 30 is as follows.

The command saturation block 31 receives the input test signal $u_N$ and outputs a limited test signal u which is a temporal signal representing the stimulation signal but with its parameters (e.g. amplitude $u_{Na}$, pulse-with $u_{Np}$ and frequency $u_{Nf}$) limited to be within a clinically safe range to generate the actual stimulation pulse. For example, the limited test signal u characterised by its amplitude $u_a$, pulse-with $u_p$ and frequency $u_f$.

The limited test signal u is input to a stimulation effect block 32 that models the temporal evolution of the building of the stimulation effect state variable $x_E$. To increase simulation speed, it is possible to use the stimulation pulse action $u_{PA}$ (input) represented by the (mathematical) multiplication of the three stimulation parameters, instead of the actual stimulation pulse u (explained further down). This function is characterised by its steady-state gain $k_E$, time constant $\tau_E$ and a continuous-time first-order differential equation.

The output of the stimulation effect block 32 is input to a modulation dynamics block 33 that models the state variable (output) $x_D$ representing the dynamic beta modulation evolution/response function to the stimulation parameters. This function is also represented by a continuous time-varying first-order system characterised by its time-varying steady-state gain $k_D(t)$ and time-varying time constant $\tau_D(t)$.

The stimulation effect block 32 and the modulation dynamics block 33 therefore form two cascaded differential stages (being first order in this example) with time constants of different orders of magnitude. In particular and as described in more detail below, the time constant of the stimulation effect block 32 represents the low pass response of neural membranes of neurons to the stimulation signal and the time constant of the modulation dynamics block 33 represents the dynamic response of a gross average of the beta band signal to the stimulation signal.

The stimulation effect block 32 and the modulation dynamics block 33 together apply a gain of the modulation with respect to plural parameters of the stimulation signal as described in detail below.

The output of the modulation dynamics block 33 is input to a modulation saturation block 34 that models the state variable (output) $x_S$ representing the limited modulation as a response to the stimulation parameters, using a Wiener function. The modulation dynamics block 33 represents a saturation of the modulation at a magnitude that is dependent on plural parameters of the stimulation signal, for example each of amplitude $u_a$, pulse-with $u_p$ and frequency $u_f$.

That said, the use of two cascaded differential stages (i.e. the stimulation effect block 32 and the modulation dynamics block 33 in this example) is not essential. As an alternative, a block performing a single first order differential function could be used instead. For example, the stimulation effect block 32 may be omitted.

The output of the modulation saturation block 34 is input to a modulation algebraic block 35 that outputs the modulation signal $\rho_\beta$, modelling the static algebraic relationship between the degree of modulation represented by the modulation signal $\rho_\beta$ and the three stimulation parameters amplitude $u_a$, frequency $u_f$ and pulse-with $u_p$. This may for example be an algebraic decrease, for example an exponential decrease. It is also possible to position this algebraic function before the modulation dynamics block 33, and adapt its relationship with an appropriate function.

The modelling unit also includes an external disturbance signal generator 36 that generates an external disturbance signal w representing external disturbances to the beta band signal. As described below, these external disturbances represented by the external disturbance signal w include artefacts of the stimulation signal on the signal measured from the human or animal body; DC-drift bias; electrocardiogram artefacts; and electrical noise. The modulation unit 40 includes an adder 41 that adds the external disturbance signal w to the emulation signal $\tilde{y}_{\beta_{LFP}}$, to provide a modified emulation signal $\hat{y}_{\beta_{LFP}}$. The use of the external disturbance signal generator 36 is not essential, but is advantageous in that the modified emulation signal $\hat{y}_{\beta_{FP}}$ produced thereby better reflects the output of a practical stimulation system.

The basis of the model implemented in the modelling unit 30 will now be discussed.

Figure 3:
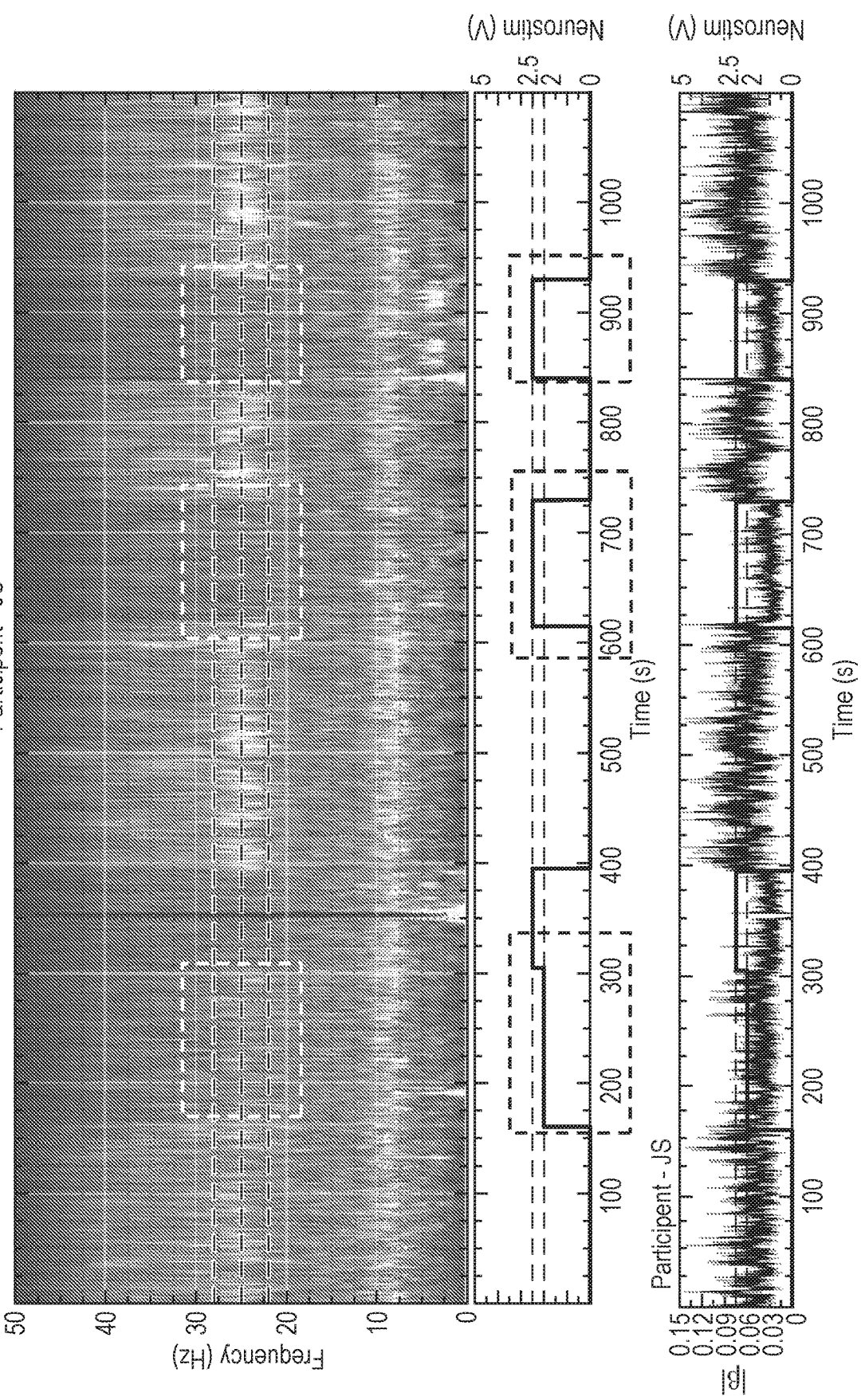
FIG. 3 is a set of plots illustrating the power spectral response and LFP signal derived under the influence of a DBS stimulation signal from an actual participant.

Many research studies have reported a decrease of the beta band signal (15-30 Hz) recorded in the STN when standard high frequency electrical DBS is applied in the same area to treat Parkinson's disease (PD). In previous studies, the average of the beta band signal decreased when the system reached steady state was quantified via the power spectrum. This is illustrated in FIG. 3 which shows the standard power spectral response (upper plot) to stimulation pulses having increasing amplitude (middle plot) and the resultant LFP (lower plot) from the right STN obtained from a male participant with PD. The amplitude of the electrical stimulation was varied with a constant stimulation frequency of 130 Hz and a constant pulse-width of 60 µs. The LFP was then filtered, and the power was estimated using a wavelet transform. FIG. 3 shows a visible decrease in the power of beta band signal when DBS is turned on at different voltage amplitudes (enclosed in boxes in FIG. 3).

Figure 4:
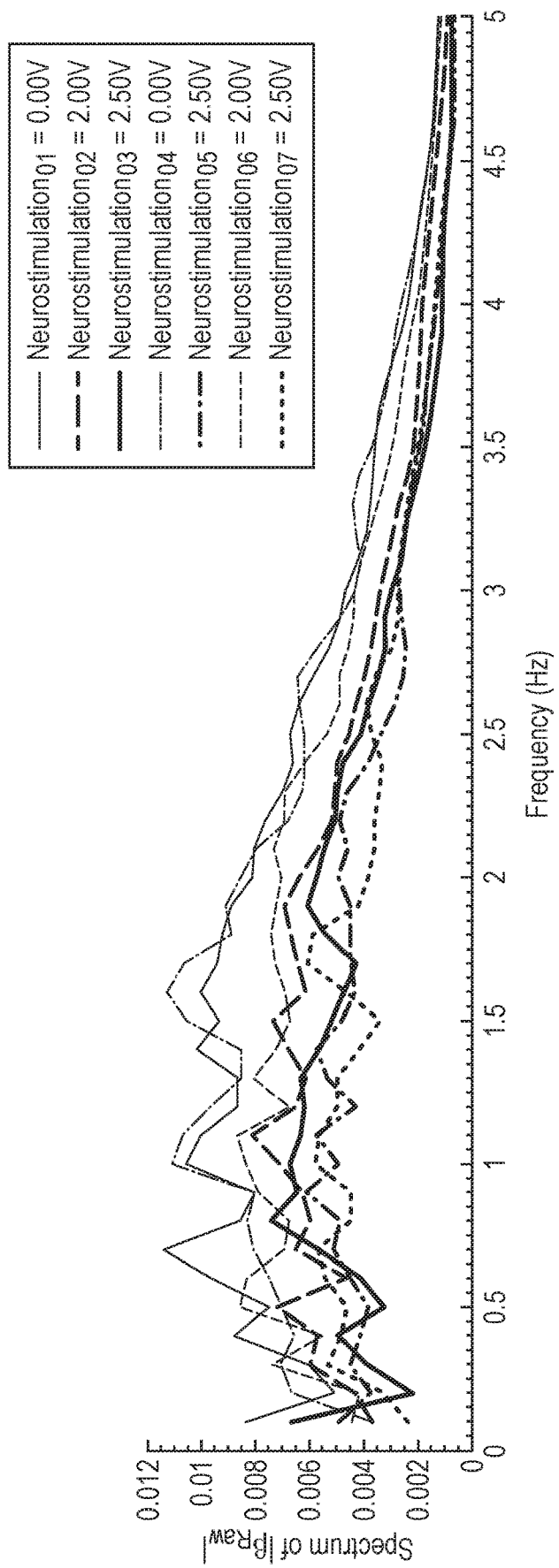
FIG. 4 is a graph of the power spectrum of an envelope of the beta band signal response to DBS at different voltage amplitude.

The dynamics and frequency components of the power of the beta band signal was investigated, applying the wavelet transform, were investigated. The dynamics of the power changed with the amplitude of the stimulation pulses as shown in FIG. 4. It can be seen that the frequency content of the beta envelope ranges between 0 and 5 Hz with a peak around 1 to 1.5 Hz. Most importantly, there is a relationship between the level of beta envelop reduction obtained and the amplitude of the stimulation applied. That is, the higher the stimulation amplitude, the higher is the observed decrease in power of the beta band signal (light to dark lines in FIG. 4 correspond to low to high amplitude stimulation, respectively).

Thus, it can be seen how the stimulation signal modulates the beta band signal. This modulation is modelled within the modelling unit 3 as follows.

Based on a study of the results from Qian et al. [Reference 3], the present inventors have concluded that a linear static relationship is satisfactory for the aim to represent the relationship between the log transformed beta reduction $\rho_{\beta_{(dB)}}$ and the three stimulation pulse parameters: amplitude $u_a$, frequency $u_f$ and pulse-with $u_p$ within a certain tested range, when these parameters were tested independently while the other two parameters were kept constant.

In this regard, three plausible candidate models were considered for describing the relationship between the stimulation pulse parameters and the degree of modulation represented by the modulation signal $\rho_{\beta_{(dB)}}$. This relationship (log transformed) is given by equation (1):

$$\rho_{\beta_{(dB)}} \triangleq 10 \cdot \log_{10}\left(\frac{P_{\beta_S}}{P_{\beta_I}}\right) \triangleq 20 \cdot \log_{10}\left(\frac{V_{\beta_S}}{V_{\beta_I}}\right) \tag{1}$$

In equation (1), $P_{\beta_I}$ is the initial beta band power measured before stimulation (when the stimulator is OFF), and $P_{\beta_S}$, the beta power measured during stimulation (when the stimulator is ON).

Model 1 assumes that the beta reduction is a linear sum of the stimulation parameters with no interaction between the stimulation parameters and shown in equation (2).

$$\rho_{\beta_{m1}}(u_p, u_f, u_p) = c_0 - (g_p \cdot u_p + g_p \cdot u_p + g_f \cdot u_f) \tag{2}$$

In equation (2) $c_0$ is the intersect, and g the constant gain associated with each pulse parameter contributing to the overall beta reduction induced by the stimulation. Model 2 assumes that beta reduction is related to the product of the three stimulation parameters equation (3).

$$\rho_{\beta_{m2}}(u_a, u_f, u_p) = c_0 - g_s \cdot u_p \cdot u_p \cdot u_f \tag{3}$$

Model 3 is based on the hypothesis that the beta reduction is linearly related to the electrical energy of the stimulation pulse equation (4).

$$\rho_{\beta_{m3}}(a_a, u_f, u_p) = c_0 - g_s \cdot u_a^2 \cdot u_p \cdot u_f \tag{4}$$

Model 3 is based on the Total electrical energy delivered (TEED) as proposed by Koss et al. [Reference 4] given by equation (5).

$$p_{TEED} = \frac{u_a^2 \cdot u_p \cdot u_f}{R} \tag{5}$$

In equation (5) R is the equivalent resistance "seen" by the stimulating electrode, and is encapsulated into the gain $g_s$.

Both Model 1 and Model 2 capture the linear relationship between the stimulation-induced beta reduction (log transformed) and the different stimulation parameters when they are tested independently as shown in Qian et al. [Reference 3]. Model 3 is also considered since TEED has been related to improve therapeutic window in Parkinson's disease (PD).

Figure 7:
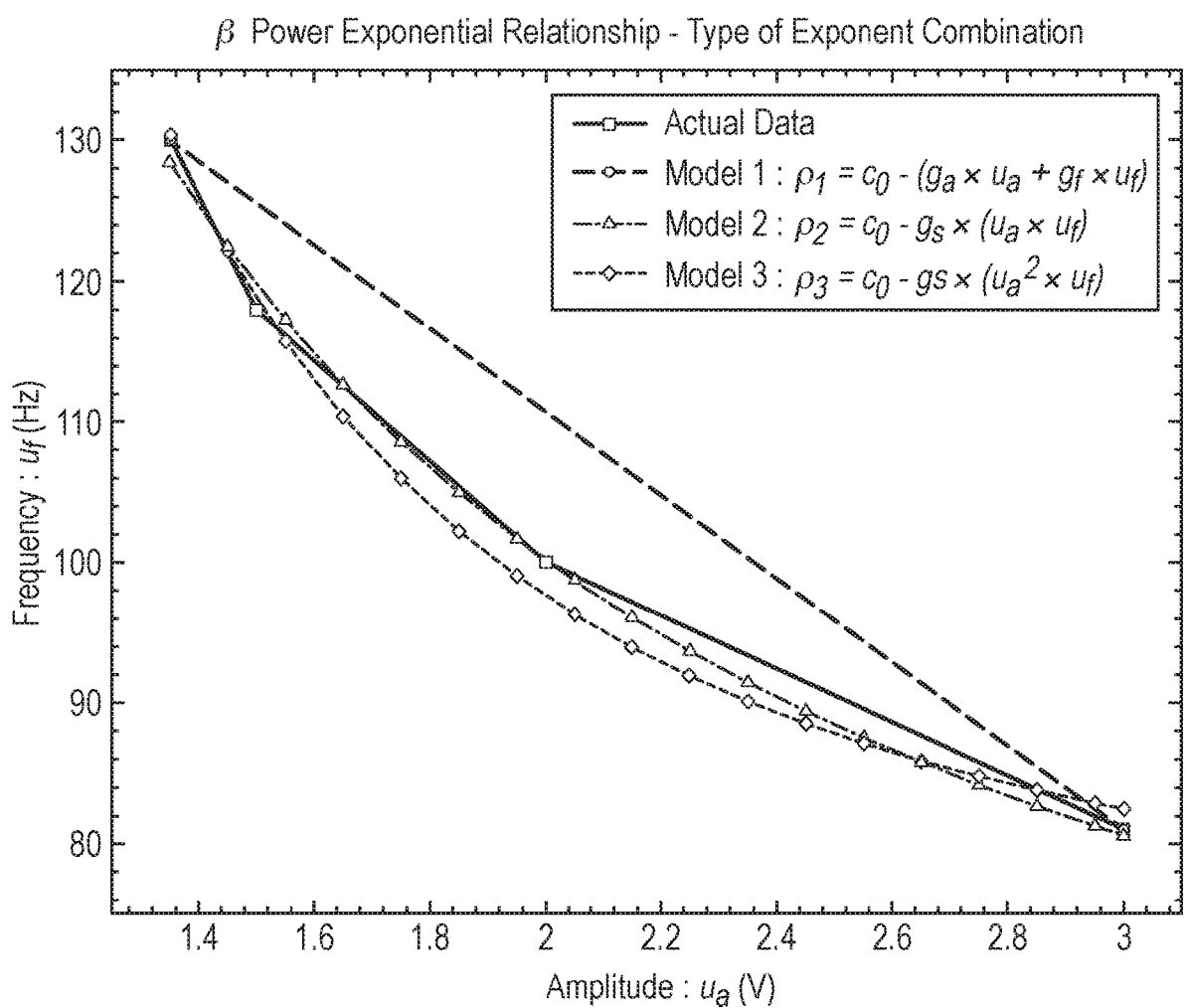
FIG. 7 is a graph of frequency against amplitude for the three models for a constant beta power reduction of −1.5 dB.
Figure 8:
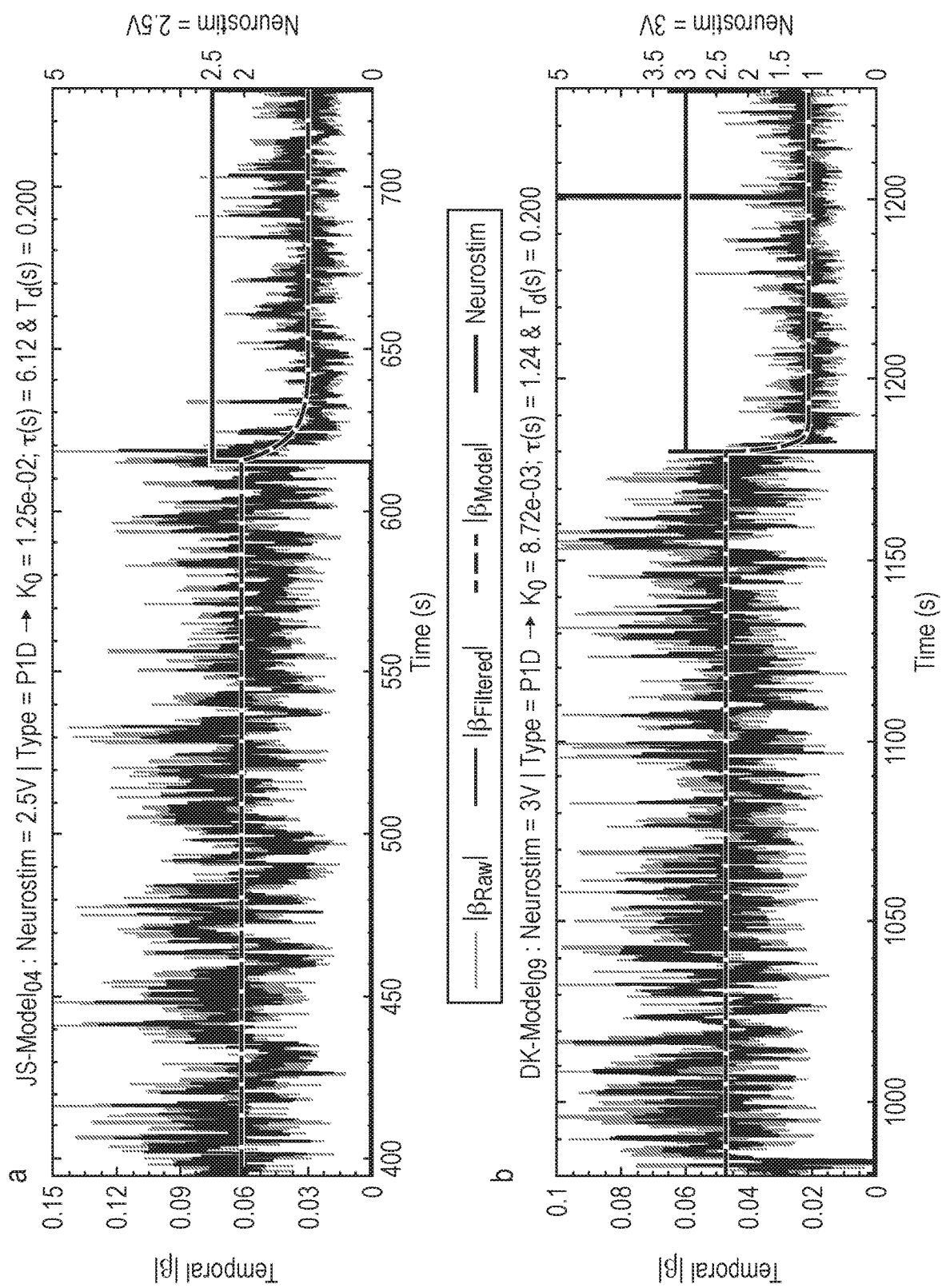
FIG. 8 are graphs of the beta band signal measured from three participants with PD in response to a step change in stimulation amplitude.
Figure 8:
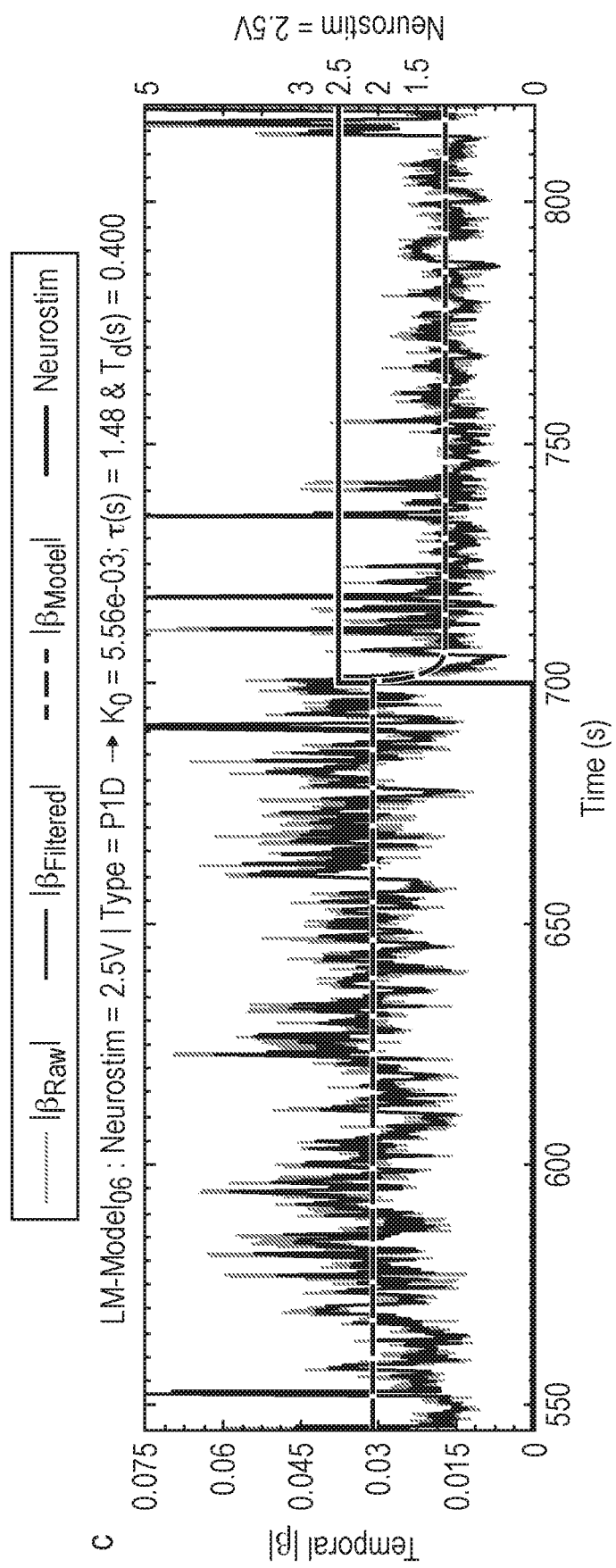
Figure 9:
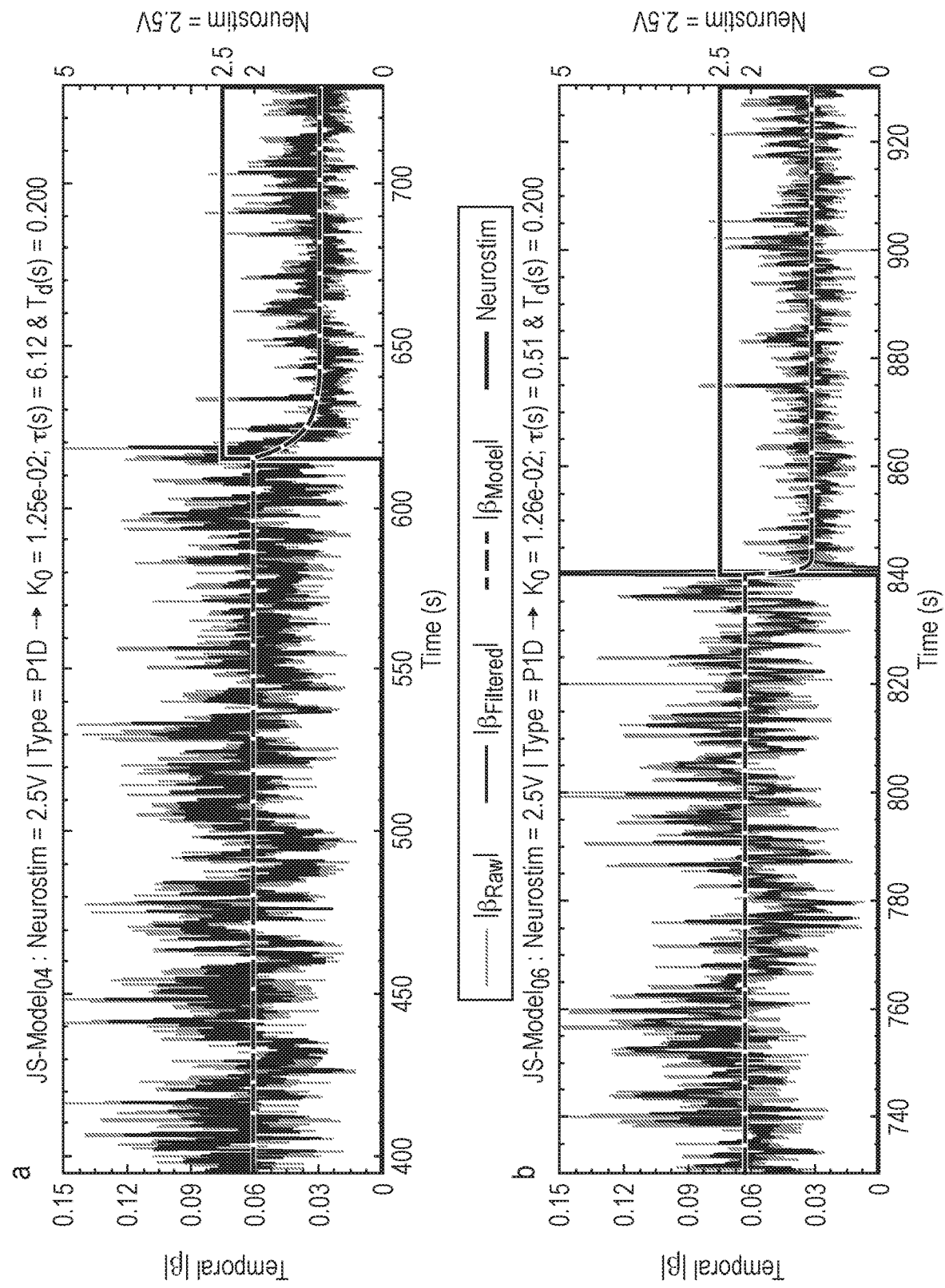
FIG. 9 are two graphs of the beta band signal measured from two participants with PD in response to a step change in stimulation amplitude.

The goodness of fit and prediction accuracy was used to evaluate how the three candidate models capture the results described in Qian et al. [Reference 3]. 66 data points in total were extracted from the linear regions (ignoring saturating data from lower or higher stimulation parameters) from FIGS. 7, 8 and 9 of [Reference 3]. These included 18 data points with the stimulation amplitude ranging between 1.3 V and 3.0 V averaged across 21 participants, where a constant stimulation frequency of 130 Hz and pulse-width of 60 µs is assumed (FIG. 7 of [Reference 3]); 15 data points (from each sub-figure) with the stimulation frequency ranging between 80.0 Hz and 120.0 Hz averaged across 14 participants, with constant stimulation amplitude at 1.5, 2.0 and 3.0 V, and a pulse-width of 60 µs (from FIG. 8 of [Reference 3]) is assumed; and 33 extra data points (17 from the 60 µs pulse-width graph and 16 for the 90 µs graph) with the stimulation amplitude ranging between 1.3 V and 2.9 V (2.8 V for the 90 µs graph due to saturation at 3.0 V) averaged across 6 participants, where a constant stimulation frequency of 130 Hz is assumed. Using the Matlab function fitnlm designed for fitting nonlinear models, and with robust fitting enabled, the three model structures were fitted to these 66 data points.

The 'leave-one-out' cross-validation method was used to evaluate the prediction accuracy of each model fitted in the previous stage. To do this, in each iteration 65 data points were selected to estimate the model parameters, and the remaining single data point was used to test the predictive power of the model. This process was repeated 66 times for each model separately, so each data point was used for testing only once. Finally, the correlation coefficient $R^2$, adjusted for number of parameters, between the model-predicted value and the measured value, the mean prediction error $\bar{\varepsilon}$ and the standard deviation (SD) of the prediction error $\mu_\varepsilon$ of the three models were quantified and compared. The results are given in Table 1:

| | Model 1 | Model 2 | Model 3 |
|---|---|---|---|
| Equation | $c_0 - \begin{pmatrix} g_a \cdot u_a + \\ g_p \cdot u_p + \\ g_f \cdot u_f \end{pmatrix}$ | $c_0 - g_s \cdot u_a \times u_p \cdot u_f$ | $c_0 - g_s \cdot u_a^2 \times u_p \cdot u_f$ |
| Parameters | $c_0 \cong +10.59$ $g_a \cong -2.5075$ $g_p \cong -6.8 \times 10^4$ $g_f \cong -0.02$ | $c_0 \cong +2.47$ $g_s \cong +269.75$ | $c_0 \cong +0.84$ $g_s \cong +79.02$ |
| Adjusted $R^2$ & p-value | 0.61 $p \leq 2.67 \times 10^{-12}$ | 0.64 $p \leq 6.53 \times 10^{-16}$ | 0.62 $p \leq 3.07 \times 10^{-15}$ |
| Mean error $\bar{\varepsilon}$ | 0.050 | 0.069 | 0.059 |
| Error SD: $\mu_\varepsilon$ | 1.388 | 1.294 | 1.317 |

The comparison revealed that Model 2, in which the beta reduction is linearly related to the product of the three stimulation parameters, provides the simplest relationship and best data fitting, with a predicting power of $R_2^2 \cong 0.64$; $p \leq 6.53 \times 10^{-16}$, whiles Model 1 has prediction capacity of $R_1^2 \cong 0.61$; $p \leq 2.67 \times 10^{-12}$, and Model 3 has a $R_3^2 \cong 0.62$; $p \leq 3.07 \times 10^{-16}$ (c.f. Table 1). However, those values are closed to each other mainly because the number of data points available is relatively small given that all three models have three variables.

Figure 5:
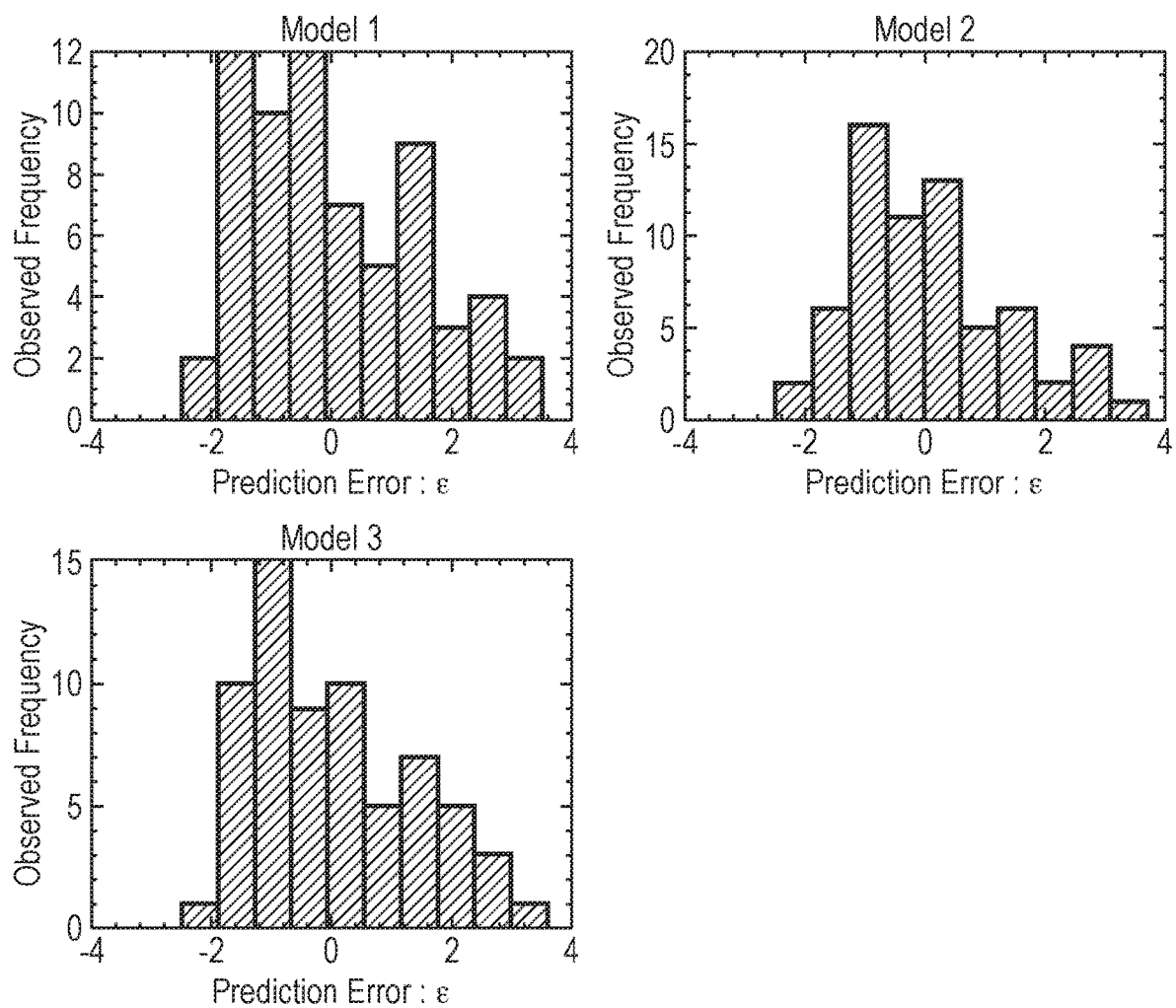
FIG. 5 is a set of histograms of prediction errors of three models for modulation of a beta band signal under the influence of a stimulation signal.
Figure 6:
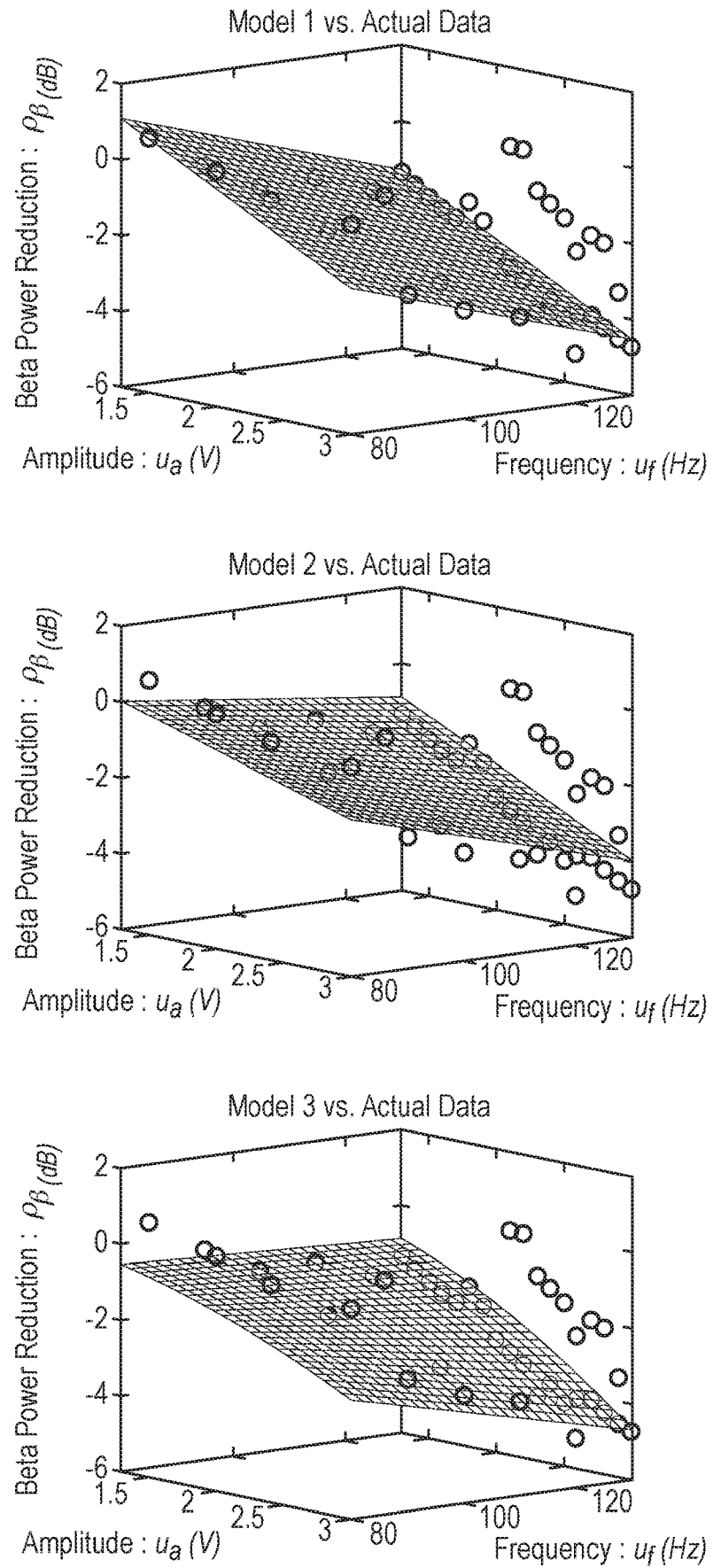
FIG. 6 is a set of plots of prediction accuracy of the three models vs. the actual data.

Furthermore, the analysis of the prediction error $\varepsilon$ in FIG. 5 shows that it is almost normally distributed for Model 2, whiles being slightly positively skewed for the two other models. Table 1 shows that the Model 2 has a mean prediction error $\bar{\varepsilon}_2 \cong 0.069$, whereas Model 1 and Model 3 have a mean value of $\bar{\varepsilon}_1 \cong 0.050$ and $\bar{\varepsilon}_3 \cong 0.059$ respectively; values that are very closed to each other. The prediction accuracy of these three models with respect to the amplitude $u_a$ and frequency $u_f$, and at constant pulse-with $u_p = 60$ µs, can be evaluated in FIG. 6 (wherein the mesh is the prediction, the dark circles are the actual data, and the light circles are the data behind the predicted mesh).

In addition to this quantitative analysis, a qualitative analysis has been conducted to further support the choice of one of these three proposed models. To this end, the situation was considered where a constant beta power reduction of $\rho_{\beta_c} = 1.5$ dB, which is a value existing in all figures of [Reference 3]. Since there is not enough data for the pulse-width $u_p$, only the effect of the amplitude $u_a$ and frequency $u_f$ parameters was considered for this purpose. In this situation, the pulse-width is taken to be constant $u_p = 60$ µs, and the three models are written as given by equations equation (2), (3) and (4) in their updated expression in equation (6).

$$\rho_{\beta_{m1}}(u_a, u_f) \cong c_0 - (g_a \cdot u_a + g_f \cdot u_{f_1})$$

$$\rho_{\beta_{m2}}(u_a, u_f) \cong c_0 - g_s \cdot u_a \cdot u_{f_2}$$

$$\rho_{\beta_{m3}}(u_a, u_f) \cong c_0 - g_s \cdot u_a^2 \cdot u_{f_3} \quad (6)$$

The values of amplitude and frequency required to achieve the constant beta power reduction of $\rho_{\beta_c} = 1.5$ dB are considered. Four pairs of data points have been estimated directly from FIGS. 7, 8 and 9 of [Reference 3], which lead to the desired constant beta power reduction of $\rho_{\beta_c} = 1.5$ dB as shown in equation (7).

$$[u_f \quad u_a] = \begin{vmatrix} 130 & 1.35 \\ 118 & 1.50 \\ 100 & 2.00 \\ 81 & 3.00 \end{vmatrix} \quad (7)$$

The relationship between the frequency $u_f$ and the amplitude $u_a$ is shown in FIG. 7, when the modulation is equal to $\rho_{\beta_c} = 1.5$ dB.

From equation (6), the frequency $u_f$ can be expressed as a function of the amplitude $u_a$ for the three candidate relationships as given by equation (8).

$$(\rho_{c_1} - c_0) = -g_a \cdot u_a - g_f \cdot u_{f_1} \quad (8)$$

$$(\rho_{c_2} - c_0) = -g_s \cdot u_a \cdot u_{f_2}$$

$$(\rho_{c_3} - c_0) = -g_s \cdot u_a^2 \cdot u_{f_1}$$

$$\Rightarrow u_{f_1} = -\frac{(\rho_{c_1} - c_0)}{g_f} - \frac{g_a}{g_f} \cdot u_a$$

$$\Rightarrow u_{f_2} = -\frac{(\rho_{c_2} - c_0)}{g_s} \cdot \frac{1}{u_a}$$

$$\Rightarrow u_{f_3} = -\frac{(\rho_{c_3} - c_0)}{g_s} \cdot \frac{1}{u_a^2}$$

The first relationship is a straight line between the frequency $u_f$ and the amplitude $u_a$, whereas the second is a 1/x and the third a $1/x^2$ relationship. In order to fit these models onto our current data, general forms are taken as given by equation (9), and then the optimal fit for these three cases is computed numerically (using the 'fit' function from Matlab), as shown in FIG. 7.

$$u_{f_1} = a \cdot u_a + b \quad (9)$$

$$u_{f_2} = \frac{a}{u_a} + b$$

$$u_{f_3} = \frac{a}{u_a^2} + b$$

FIG. 7 shows that the actual data seems to follow closely Model 2 represented by a 1/x relationship; whereas, the model 1 based on a straight line is clearly a poor fit. The last analysis is to evaluate the slope between the beta reduction $\rho$ and the stimulation amplitude $u_a$ by taking the partial derivative with respect to the stimulation amplitude $u_a$ of Model 2 & 3 given by equation (6) when the frequency $u_f$ is kept constant; the slopes of both models are given on equation (10).

$$\frac{\partial \rho_{\beta_{m2}}}{\partial u_a} = \Delta_{\rho_2} = -g_s \cdot u_f^\eta \quad (10)$$

$$\frac{\partial \rho_{\beta_{m3}}}{\partial u_a} = \Delta_{\rho_3} = -2 \cdot g_s \cdot u_a \cdot u_f^\eta = 2 \cdot \Delta_{\rho_2} \cdot u_a$$

From equation (10), Model 2 implies a constant slop, whiles Model 3 implies that the slope is proportional to the amplitude of the stimulation, which is clearly at odds with data in FIG. 7 of [Reference 3].

Overall, Model 1, based on a linear sum of the stimulation parameters, has the poorest fit both to the actual data and to the situation where a constant beta power reduction of $\rho_{\beta_c} = 1.5$ dB is required. Model 3, based on the pulse total electrical energy, although offering a good fit, implies that the reduction slope is proportional to the amplitude of the stimulation, which is not the case. Finally, Model 2, based on the interaction of the three stimulation parameters, both offers a good data fitting and a slope consistent with currently available data. These conclusions are supported by a visual inspection of the prediction accuracy given in FIG. 6 of the these three models with respect to the amplitude $u_a$ and frequency $u_f$, and at constant pulse-with $u_p = 60$ μs.

In total, Model 2 provides the best data fitting and yet the simplest and most consistent relationship, and therefore has been chosen as the structure of the static algebraic relationship within the model implemented in the modelling unit 30 between log transformed beta modulation $\rho_{\beta_{(dB)}}$ and the three stimulation parameters of amplitude $u_a$, pulse-with $u_p$ and frequency $u_f$ as given by equation (11).

$$\rho_\beta(u_a, u_f, u_p)_{(dB)} \triangleq c_{0_{(dB)}} - g_{s_{(dB/V)}} \cdot u_{a_{(V)}} \cdot u_{p_{(s)}} \cdot u_{f_{(Hz)}} \quad (11)$$

with $c_0 \triangleq +2.4657$, $g_s \triangleq +269.7454$ $u_a > 0$, $u_f > 0$ and $u_p > 0$ The algebraic relationship implemented in the modulation algebraic block 35 will now be considered. This may for example be an algebraic decrease, for example an exponential decrease.

Modulation of the beta band signal induced by stimulation can be expressed in two related domains: the power domain where $x_{\beta_{LFP_{(dB)}}}$ is the power of the beta band LFP signal, and is particularly useful for designing and evaluating the overall functionality of the closed-loop algorithm in simulation; the voltage domain where $x_{\beta_{LFP_{(V)}}}$ is the beta band LFP voltage signal, and is particularly useful for designing and evaluating the overall functionality of the real-time closed-loop algorithm and the signal conditioner implementation (real-time estimation of the beta and extraction of its envelope).

Considering the power domain, equation (11) expresses the modulation of the beta band signal in relation to stimulation parameters in the power domain: as a ratio of power. Combining the definition of a power spectrum and equation (11) yields the identity in equation (12).

$$\rho_\beta(u_a, u_f, u_p)_{(dB)} \triangleq 10 \cdot \log_{10}\left(\frac{P_{\beta_S}}{P_{\beta_I}}\right) = c_0 - g_s \cdot u_a \cdot u_p \cdot u_f \quad (12)$$

From equation (12), $P_{\beta_I}$ is the initial beta band power measured before stimulation (when the stimulator is OFF), and $P_{\beta_S}$ the beta power measured during stimulation (when the stimulator is ON). The change of base formula allows to convert $\log_{10}$ into the natural logarithm ln as shown in equation (13).

$$\log_{10}(x) \triangleq \frac{1}{\log_e(10)} \times \log_e(x) = \frac{1}{\ln(10)} \times \ln(x) \quad (13)$$

The static power ratio relationship given by equation (12) is expressed in the natural logarithm base given by equation (14).

$$\rho_{\beta_{(dB)}} = \ln\left|\frac{P_{\beta_S}}{P_{\beta_I}}\right| = \frac{\ln(10)}{10} \cdot (c_0 - g_s \cdot u_a \cdot u_p \cdot u_f) \quad (14)$$

Taking the exponential on both sides of equation (14) leads finally to the expression of the direct relationship between beta power reduction $\rho_{\beta_P}$ in the power domain and the three stimulation parameters: amplitude $u_a$, frequency $u_f$ and pulse-with $u_p$ as shown in equation (15).

$$\rho_\beta(u_a, u_p, u_f)_P = \frac{P_{\beta_S}}{P_{\beta_I}} = e^{(k_{0_P} - k_{s_P} \cdot u_a \cdot u_p \cdot u_f)} = \rho_{\beta_{0_P}} \cdot e^{-k_{s_P} \cdot u_a \cdot u_p \cdot u_f} \quad (15)$$

$$\Rightarrow P_{\beta_S} = P_{\beta_I} \cdot \rho_{\beta_{(dB)}} = P_{\beta_I} \cdot \rho_{\beta_{0_P}} \cdot e^{-k_{s_P} \cdot u_a \cdot u_p \cdot u_f}$$

with $k_{0_P} = \frac{\ln(10)}{10} \cdot c_0 \triangleq +0.5678$ $k_{s_P} = \frac{\ln(10)}{10} \cdot g_s \triangleq +62.1111$ and $\rho_{\beta_{0_P}} = e^{k_{0_P}} \triangleq +1.7643$ Alternatively, the definition of the relative power used in spectral analysis may be converted into the voltage domain. This time as a ratio of voltage is shown by equation (16)

$$\rho_\beta(u_a, u_f, u_p)_{(dB)} \triangleq 10 \cdot \log_{10}\left(\frac{P_{\beta_S}}{P_{\beta_I}}\right) \tag{16}$$

$$\triangleq 20 \cdot \log_{10}\left(\frac{V_{\beta_S}}{V_{\beta_I}}\right)$$

Similarly, equation (16), $V_{\beta_I}$ is the initial beta band voltage measured before stimulation (when the stimulator is OFF), and $V_{\beta_S}$ the beta voltage measured during stimulation (when the stimulator is ON). Using equations (12) to (15), the direct relationship between beta reduction $\rho_{\beta_V}$ in the voltage domain and the three stimulation parameters of amplitude $u_a$, frequency $u_f$ and pulse-with $u_p$ is shown in equation (17).

$$\rho_\beta(u_a, u_p, u_f)_V \triangleq \frac{V_{\beta_S}}{V_{\beta_I}} = e^{(k_{0_V} - k_{s_V} \cdot u_a \cdot u_p \cdot u_f)} = \rho_{\beta_{0_V}} \cdot e^{-k_{s_V} \cdot u_a \cdot u_p \cdot u_f} \tag{17}$$

$$\Rightarrow V_{\beta_S} = V_{\beta_I} \cdot \rho_{\beta_{0_V}} \cdot e^{-k_{s_V} \cdot u_a \cdot u_p \cdot u_f}$$

$$\text{with } k_{0_V} = \frac{\ln(10)}{20} \cdot c_0 \cong +0.2839$$

$$k_{s_V} = \frac{\ln(10)}{20} \cdot g_s \cong +31.0556$$

$$\text{and } \rho_{\beta_{0_V}} = e^{k_{0_V}} \cong +1.3283$$

From this stage, when $k_0$, $k_S$, $\rho_{\beta_0}$ and $\rho_\beta$ are mentioned without their associated indices, either the power or voltage domains is meant.

The dynamics of the modulation of the beta band signal are now considered.

So far, there have been presented the algebraic relationships governing the steady-state behaviour of the modulation of beta band signal due to the stimulation parameters amplitude $u_a$, pulse-with $u_p$ and frequency $u_f$. However, the knowledge of the time course of the beta attenuation allows more sophisticated control algorithms that can optimise for reduced side effects and energy consumption for instance.

Data processing for dynamic modelling is considered as follows. To achieve this objective, STN LFPs were recorded from five participants with Parkinson's disease (PD) who were implanted with electrodes for deep brain stimulation (DBS). Standard electrical stimulation with a pulse-width $u_p$=60 μs, frequency $u_f$=130 Hz and with different amplitudes $u_a$ was applied in an on-off fashion to evaluate the 'step' response of beta reduction to stimulation. The step response was also obtained by increasing the stimulation amplitude step by step with several minutes between each step change.

A notch filter (based on the filtfilt function in Matlab) centred at 50 Hz with a Q-factor of 30 was used in order to remove the artefact due to the mains. Then, the LFP signal was filtered with a second order Butterworth high-pass filter of 1 Hz to remove any DC component. This was followed by a second order Butterworth low-pass filter of 50 Hz to remove the frequencies above the beta band of interest. Then, the power spectrum of the filtered signal was computed using a standard wavelet transform approach, with 1 Hz frequency resolution (FIG. 3). Then, the frequencies components that were close to the peak beta frequency were added together. For participant 1, the frequency components between 22 and 28 Hz were summed. For participant 2, frequency components between 22 to 32 Hz were summed. For participant 3, frequency components between 15 and 30 were summed.

FIG. 8 shows an example of the step response of the beta band observed when DBS was switched ON in the three participants. It took several seconds before beta reached its reduced steady-state or static value.

Dynamic modelling considerations are as follows.

The main objective is to propose a model allowing the design and implementation of (dynamic) closed-loop control algorithms. Such a model is required to be close enough to the practical clinical situation where (temporal) electrical stimulations lead to temporal evolution of the beta reduction. In another words, the model is between the actual electrical stimulation pulses u from the output of the neurostimulator with a time scale in microsecond, and the beta $\rho_\beta$ measured from the local field potential (LFP) with a time scale in seconds. Thus, the goal is to propose a framework allowing to transpose (almost) directly the design and implementation of the control algorithm based on simulation and emulation, to the patient with minimal, if any, change.

To this end, two cascaded first-order differential dynamical functions $H_E$ and $H_D$ are implemented to simulate the temporal evolution of the beta envelop responses to electrical stimulation (the use of a single first-order differential dynamic function is also possible), as follows.

A linear first-order continuous-time model $H_E$ is implemented within the stimulation effect block 32 to describe the building up of the 'stimulation effect' $x_E$ that defines the steady-state value or static beta reduction that will be reached after some times (several seconds) following the start of the stimulation. This model is used to represent the 'conversion' of the actual temporal train of electrical stimulation pulses into an 'effect' that will then drive the slow temporal beta reduction exemplified in FIG. 8 and represented by the transfer function $H_D$.

The transfer function $H_E$ represents proximal and fast reactions to the stimulation pulses, whereas the transfer function $H_D$ is used to represent more distal network wide and slow phenomena. Thus, the transfer functions $H_E$ and $H_D$ have time constants of different orders of magnitude.

This approach is consistent to a physiologically based mean-field model of the basal ganglia-thalamocortical system (BGTCS) shown to account to a good level for some electrophysiological correlates of Parkinson's disease (PD) [Reference 10], [Reference 11]. Van Albada and Robinson capitalised on modelling work carried out over more than half century by a large community of researchers to propose their mean-filed approach using a linear second-order damped-wave equation to model at neurone level local transmission of information, and a linear first-order equation to model information processing at distal level between neural population which uses a second order damped-waves equation to model propagation waves [Reference 10], [Reference 11]. In taking the past work modelling into account, we have simplified it to use two linear first order equations: a linear first-order continuous-time model $H_E$ to account for local neural processing, and a linear first-order continuous-time model $H_D$ to account for more distal network-wide and slow phenomena. In doing so, we need to assume that the primary first-order model $H_E$ has a time constant compatible with the time duration of the pulses in order for its output to reach a steady-state value, here called an 'effect', that is directly proportional (direct product) to the stimulation parameters, and would remain stable for stable stimulation parameters. Therefore, the time constant of the primary first-order model $\tau_E$ has to be necessary much shorter than the time constant $\tau_E$ observed on the more distal behaviour of beta envelop response to stimulation (cf. FIG. 8), represented by the second first-order system given by the transfer function $H_D$ (c.f. below).

Conveniently the transfer function $H_E$ of the 'stimulation effect' $x_E$ given by equation (18) is defined in the Laplace domain $\mathcal{L}$ [Reference 5], where s represents the Laplace variable, $x_E$ the state variable (output) that defines the steady-state value of the beta envelop responses to electrical stimulation, u the electrical stimulation as the control variable (input) of the stimulation effect, $k_E$ the steady-state gain and $\tau_E$ the time constant of the stimulation effect evolution in response to the stimulation u.

$$H_E(s) = \frac{x_E(s)}{u(s)} = \frac{k_E}{\tau_E \cdot s + 1} \quad (18)$$

with $\tau_E \ll \tau_D$ where '(t)' denotes a continuous-time variable, and $t \in \mathbb{R}^+$ throughout this document. Expanding the Laplace equation (18), and taking the inverse Laplace Transform $\mathcal{L}^{-1}$ from both sides leads to its differential temporal form in equation (19) required for further modelling and practical implementation [Reference 5].

$$\dot{x}_E(t) + \frac{1}{\tau_E} \cdot x_E(t) = \frac{k_E}{\tau_E} \cdot u(t) \quad (19)$$

The model given by equations (18) and (19) hypothesises that the stimulation effect has a (proportional) linear relationship with the stimulation pulse parameters as defined by equation (14) when the stimulation frequency is comprise within the linear range (70 Hz≤$u_f$≤130 Hz). The choice of a first order low-pass system of equations (18) and (19) is further consolidated by the fact the intrinsic lowpass filtering of electrical stimulation signals by neural membrane is likely to be a universal property displayed by neurons; this lowpass filtering behaviour prevent neurons to follow a high stimulation frequency [Reference 6], [Reference 7].

Moreover, in the previous section looking at the static relationship of stimulation-induced beta modulation, it is shown that Model 2, postulating that beta reduction is related to the direct product of the three stimulation parameters, is the best out of the three proposed models to represent the structure of our static algebraic relationship between beta power modulation $\rho_{\beta_p}$ and the stimulation parameters given by equation (11). As only the positive alternance of the stimulation pulse is the 'active' part that leads to beta reduction (the negative part is used for charge balance), it can be considered that the input of the primary transfer function of the stimulation effect $H_E$ has a shaped of a square-wave signal with a very small duty-cycle. In the standard situation this will be a positive pulse of 60 µs with a period of 1/130≅7.7 ms, thus leading to a duty-cycle of roughly 0.0078. If there is used a first-order model with a time constant compatible with the duration of the stimulation pulses and this duty-cycle, the output $x_E$ will reach an average value which is directly proportional on the product of the three stimulation parameters: amplitude $u_a$, frequency $u_f$ and pulse-with $u_p$ as required by equation (11). At this stage, for the efficient implementation of this model for numerical simulation, it is completely equivalent in term of steady-state behaviour to use the exact stimulation pulses as generated by an actual neurostimulator, or to take directly the product of the three parameters of the stimulation pulse: amplitude $u_a$, pulse-with $u_p$ and frequency $u_f$ as the input of $H_E$. In both cases, the steady-state value will be very close to each other, but the dynamic behaviour different, which is not relevant for our modelling goal, and would only last a very short period of time. Herein, this is called the 'combined' set of the stimulation parameters the 'pulse action' $u_{PA}$ shown in equation (20). The advantage of using this combined 'pulse action' $u_{PA}$ rather than the actual stimulation pulse u is that the simulation will be much faster. This approach is compatible with the fact that our goal is to develop control algorithms that act at hundred millisecond time scale to control the beta reduction behaviour that is in the time scale of several seconds.

$$u_{PA} = u_a \cdot u_p \cdot u_f \quad (20)$$

From now on, when reference is made to the stimulation command, the pulse action defined in equation (20) is intended unless stated. And, for simulation purpose, the time constant $\tau_E$ is set in its compatible range: 1 ms≤$\tau_E$≤100 ms. In this implementation, $\tau_E$=10 ms is chosen.

The dynamic model structure is now considered.

A second first-order model is used to simulate the response of the beta envelop $\rho_\beta$ to the stimulation effect $x_E$, with a time constant $\tau_D$ supposed to be the dominant time constant (dominant pole); thus, with a duration much longer than the primary first-order system $H_E$:$\tau_D \gg \tau_E$. This second system is represented by the dynamic transfer function $H_D$ given in equation (21) in the Laplace domain $\mathcal{L}$ [Reference 5]; where s represents the Laplace variable, $x_D$ the state variable (output) of the dynamic beta modulation evolution/response function to stimulation effect $x_E$ as the control variable (input), $k_r$, the steady-state gain and $\tau_D$ the time constant of the beta envelop evolution in response to the stimulation effect $x_E$ (and subsequently the response to the stimulation pulse u).

$$H_D(s) = \frac{x_D(s)}{x_E(s)} = \frac{k_D}{\tau_D \cdot s + 1} \quad (21)$$

The transfer function given in equation (21) is represented in its expanded Laplace form in equation (22).

$$x_D(s) \cdot (\tau_D \cdot s + 1) = k_D \cdot x_E(s) \quad (22)$$

Taking the inverse Laplace Transform $\mathcal{L}^{-1}$ [Reference 5], from both sides of equation (22), leads to its differential temporal form in equation (23) required for further modelling and practical implementation.

$$\dot{x}_D(t) + \frac{1}{\tau_D} \cdot x_D(t) = \frac{k_D}{\tau_D} \cdot x_E(t) \quad (23)$$

Such a situation to cascade two first-order systems is classical in control applications: the first leading the second with typically the time constant of the first system being negligible compare to (much shorter than) the second, in order for the first system to establish its action before being able to drive the output of the second system. This is essentially the approach adopted where the "stimulation effect" function $x_E$ has a time constant $\tau_E$ much shorter than the time constant $\tau_D$ of the "stimulation dynamics" function $x_E$. Therefore, the total dynamic response of the beta envelop $x_E$ now in response to the electrical stimulation pulse action $u_{PA}$ can be represented by the transfer function $H_{ED}$ given in equation (24).

$$H_{ED}(s) = \frac{x_D(s)}{u_{PA}(s)} = H_E(s) \cdot H_D(s) \qquad (24)$$
$$= \frac{k_E}{\tau_E \cdot s + 1} \times \frac{k_D}{\tau_D \cdot s + 1}$$
$$= \frac{k_E \cdot k_D}{\tau_E \cdot \tau_D \cdot s^2 + (\tau_E + \tau_D) \cdot s + 1}$$

The cascaded two first-order model hypothesises that the stimulation effect $x_E$ is proportional to the pulse action $u_{PA}$ in the steady-state regime, where it stabilises quickly (within $\approx 5 \times \tau_E$) to a constant value given by equation (25).

$$\lim_{t \to \infty}(x_E(t)) \simeq k_E \cdot u_{PA} = k_E \cdot u_a \cdot u_p \cdot u_f \qquad (25)$$

Whereas the final steady-state value of the stimulation modulation is reached following the end of the second first-order dynamics with has a much longer time constant (within $\approx 5 \times \tau_D$). This final steady-state value is proportional to the static gains $k_E$ and $k_E$ of both first order systems and the pulse action $u_{PA}$ as given by equation (26).

$$\lim_{t \to \infty}(x_D(t)) \simeq k_E \cdot k_D \cdot u_{PA} = k_E \cdot k_D \cdot u_a \cdot u_p \cdot u_f \qquad (26)$$
$$= k_S \cdot u_a \cdot u_p \cdot u_f$$
$$\text{with } k_S = k_E \cdot k_D$$

In implementing the model, for convenience from equation (26) there has been set $k_S = k_E \Rightarrow k_E = 1$, which allow us to account for variation of the gain $k_S$ by a direct percentage of variation of $k_D$.

The Matlab function procest may be used to identify the model parameters of the continuous-time transfer function given by equation (24). Since the time constant $\tau_E$ of the first pole has been set to be negligible in comparison to the dominant pole $\tau_D$, for the actual identification procedure a first-order model is fitted because the intention is to get an estimate of the order of magnitude of the time constant $\tau_D$ rather than an accurate value. Fitting a second-order transfer function leads to an over-dumped dual-pole each having a time constant roughly half that of a first-order transfer function, their sum being very close to it. FIG. 8 shows examples of such a model using equation (21) fitted onto each patient's step response data (being the light lines). A total of 13 step responses were measured from five participants with an average time constant $\tau_D \cong 2.94$ s±3.85 s. The large standard deviation in the time constant is indicative of non-normal distribution. The time delay $T_D$ found is essentially due to the ramping of the stimulation amplitude to avoid side effects, and is not taken into consideration in the model.

A rapid variation is seen within the same participant in the time constant $\tau_D$ (from 6 to 0.5 second) over a short period of time (less than 5 minutes in our case), for example as shown in FIG. 9 while the static gain remained constant. In addition, a relatively rapid variation of steady-state beta reduction $\rho_\beta$ for the same stimulation pulse is seen over a longer period of time. Such parameter variation has to be taken into consideration by effectively using a time-varying model rather than a time-invariant model as originally presented in equations (21) and (23). Such a time-varying model is presented in equation (27), where the time constant $\tau_D(t)$ and the gain of the stimulation modulation dynamic $k_D(t)$ are both a function of the time variable. For simplicity, it is considered that the static gain of the stimulation effect function $k_E$ remains constant. In such a case, the variation of the overall static gain $k_S$, due to a variation of the steady-state beta reduction $\rho_\beta$ for the same stimulation pulse mentioned just above, is simply assigned to the static gain $k_D$. This relatively rapid variation of the parameters of the stimulation modulation dynamic function cannot be represented with the classical Laplace transform [Reference 8]. Instead, it is directly represented in the time-varying differential equation given by equation (27).

$$\dot{x}_D(t) + \frac{1}{\tau_D(t)} \cdot x_D(t) = \frac{k_D(t)}{\tau_D(t)} \cdot x_E(t) \qquad (27)$$
$$\dot{x}_D(t) + a(t) \cdot x_D(t) = b(t) \cdot x_E(t)$$
$$\text{with } a(t) = \frac{1}{\tau_D(t)} \quad \& \quad b(t) = \frac{k_D(t)}{\tau_D(t)}$$

In summary, a second-order continuous time-varying system is used to model the temporal evolution of the beta reduction $\rho_\beta$ in response to stimulation pulses u in order to capture the main temporal features measured from patients. The time-varying time constant and static gain is unusual, and will be particularly challenging when controlling the dynamic profile of the beta reduction in real-time.

The saturation of the modulation implemented in the modulation saturation block 34 will now be considered.

It is noted that Model 2 from equation (11) and (15) is only valid within a certain range of each stimulation parameter. With a stimulation amplitude $u_a < 1.3$ V or stimulation frequency $u_f \leq u_{f_{Low}} \cong 70$ Hz, the reduction of beta power $\rho_{\beta_{(dB)}}$ obtained does not follow anymore the linear relationship established in equation (11), and seems to remain roughly constant (c.f. FIG. 8 of [Reference 3]). This indicates that a minimal stimulation voltage amplitude and frequency are required to obtain a reduction of beta. At the other extreme, when the stimulation frequency $u_f \geq u_{f_{High}} \cong 130$ Hz, beta reduction saturates to a minimum value. However, different minimum values $\rho_{\beta_{(dB)}}^{min}$ were reached for different stimulation amplitudes or pulse widths tested. This plateau value is lower for higher amplitude and pulse-width, and higher for lower values; thus, the saturation limits are dynamically dependent on the stimulation amplitude $u_a$, pulse-with $u_p$. Also, there is an obvious limitation of the three stimulation parameters to a safe clinical range.

To take into consideration these two types of limitations, a Hammerstein-Wiener model is generally used [Reference 2] as represented in FIG. 1. The stimulation parameters are first limited to a safe clinical range by a Hammerstein memoryless (nonlinear) saturation function $\hat{f}_H$ defined by equation (28).

$$u(t) = \hat{f}_H(t, u_{Na}(t), u_{Np}(t), u_{Nf}(t)) \qquad (28)$$
$$\& \hat{f}_H(t, .) = \begin{cases} u_{a,p,f}^{max} & \text{if} \quad u_{Na,p,f}(t) > u_{a,p,f}^{max} \\ u_{a,p,f}(t) & \text{if} \quad u_{a,p,f}^{min} \leq u_{Na,p,f}(t) \leq u_{a,p,f}^{max} \\ u_{a,p,f}^{min} & \text{if} \quad u_{Na,p,f}(t) < u_{a,p,f}^{min} \end{cases}$$

From equation (28), $u_{a,p,f}$ represents each stimulation parameters limited individually (6 in total): $u_a^{min}$, $u_p^{max}$ etc.

Then, to take into consideration the dynamic nonlinear response of the beta reduction to stimulation pulse, a dynamic (nonlinear) saturation function is implemented, at the output of the beta reduction model, by a dynamic Wiener memoryless (nonlinear) saturation function $\hat{f}_W$ defined by equation (29).

$$x_S(t) = \hat{f}_W(t, x_D(t), u_a(t), u_p(t), u_f(t)) \quad (29)$$

$$\text{with } \hat{f}_W(t,.) = \begin{cases} x_{S_{High}}(t) & \text{if } u_f(t) > u_{f_{High}} \\ x_D(t) & \text{if } u_{f_{Low}} \le u_f(t) \le u_{f_{High}} \\ x_{S_{Low}}(t) & \text{if } u_f(t) < u_{f_{Low}} \end{cases}$$

where $x_{S_{High}}(t) = x_{D_{High}}(t)$ & $x_{S_{Low}}(t) = x_{D_{Low}}(t)$

Figure 10:
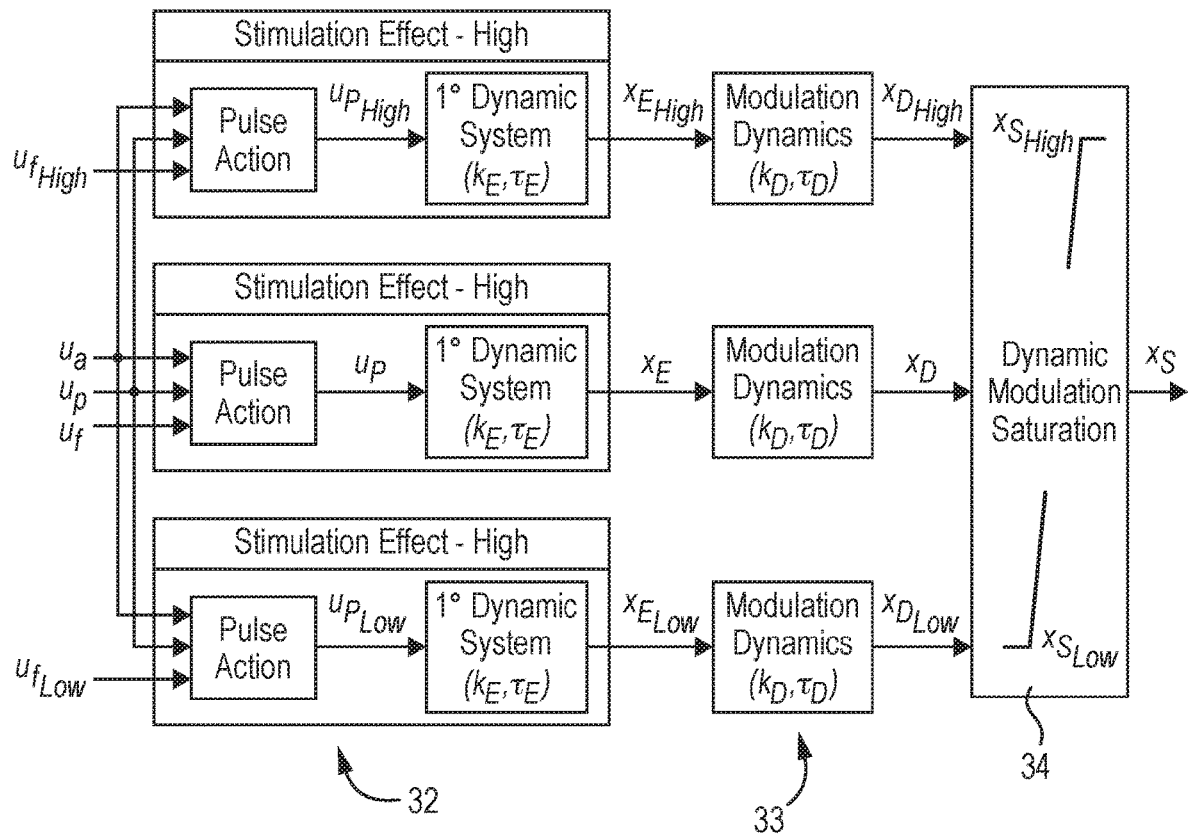
FIG. 10 is a graphical representation of a dynamic Wiener memoryless (nonlinear) saturation function.

For the practical implementation of equation (29), $x_D$, $x_{D_{High}}$ and $x_{D_{Low}}$ need to have the same dynamics for a smooth transition within the dynamic boundary of the saturated modulation signal $x_s$. As beta modulation $x_D$ in response to the stimulation parameters obeys a dynamic function (modelled here by a first-order dynamic function), since that response cannot happen instantaneously. Similarly, the establishment of the beta modulation boundaries $x_{D_{High}}$ and $x_{D_{Low}}$ cannot also happen instantaneously; it is natural to consider that these boundaries follow the same dynamic as $x_D$. Therefore, the same transfer function $H_{ED}$ is used, here (second-order given in equation (24), to derive $x_D$, $x_{D_{High}}$ and $x_{D_{Low}}$. Alternatively, its equivalent time-varying differential equation given by equation (27) may be used when considering that $H_{ED}$ are time dependent. FIG. 10 shows the structure of this dynamic Wiener memoryless (nonlinear) saturation function in more detailed way based on the case of time-invariant $H_{ED}$ for illustration; the case of time-varying, $H_{ED}$ is replaced by the time-varying differential equation given by equation (27).

In the case of the time-invariant transfer function $H_{ED}$ is written in the Laplace domain $\mathcal{L}$ [Reference 5], $x_{D_{High}}$, $x_D$ and $x_{D_{Low}}$ by equation (30), where $H_{ED}$ is given in equation (24).

$$x_{S_{High}}(s) = x_{D_{High}}(s) = H_{ED}(s) \cdot u_{PA_{High}} \quad (30)$$
$$= H_{ED}(s) \times (u_a \cdot u_p \cdot u_{f_{High}})$$
$$x_D(s) = H_{ED}(s) \cdot u_{PA}$$
$$= H_{ED}(s) \times (u_a \cdot u_p \cdot u_f)$$
$$x_{S_{Low}}(s) = x_{D_{Low}}(s) = H_{ED}(s) \cdot u_{PA_{Low}}$$
$$= H_{ED}(s) \times (u_a \cdot u_p \cdot u_{f_{Low}})$$

In the steady-state regime, $x_{D_{High}}$, $x_D$, and $x_{D_{Low}}$ are given by equation (31), where $k_S$ is defined by equation (26).

$$\lim_{t \to \infty}(x_{S_{High}}(t)) = \lim_{t \to \infty}(x_{D_{High}}(t)) \simeq k_S \cdot u_a \cdot u_p \cdot u_{f_{High}} \quad (31)$$
$$\lim_{t \to \infty}(x_D(t)) \simeq k_S \cdot u_a \cdot u_p \cdot u_f$$

$$\lim_{t \to \infty}(x_{S_{Low}}(t)) = \lim_{t \to \infty}(x_{D_{Low}}(t)) \simeq k_S \cdot u_a \cdot u_p \cdot u_{f_{Low}}$$

with $k_S = k_E \cdot k_D$

Combining equations (31), (15), and (16) the algebraic modulation boundaries is finally expressed by equation (32). Note that equation (32) is valid for both power and voltage domains, and that $\rho_{\beta_{High}}$ is defined by $x_{S_{Low}}$ and vice versa for $\rho_{\beta_{Low}}$ which is defined by $x_{S_{High}}$.

If $u_{f_{Low}} \le u_f(t) \le u_{f_{High}}$ (32)

$$x_S(t, u_a, u_p, u_f) \simeq k_S \cdot u_a(t) \cdot u_p(t) \cdot u_f(t)$$
$$\Rightarrow \rho_\beta(t, u_a, u_p, u_f) = \rho_{\beta_0} \cdot e^{-x_S}$$
$$= \rho_{\beta_0} \cdot e^{-k_S \cdot u_a(t) \cdot u_p(t) \cdot u_f(t)}$$

If $u_f(t) > u_{f_{High}} \Rightarrow x_{S_{High}}$ & If $\Rightarrow u_f(t) < u_{f_{Low}} \Rightarrow x_{S_{Low}}$ $$x_{S_{High,Low}}(t, u_a, u_p, u_{f_{High,Low}}) \simeq k_S \cdot u_a(t) \cdot u_p(t) \cdot u_{f_{High,Low}}$$
$$\Rightarrow \rho_{\beta_{High,Low}}(t, u_a, u_p, u_{f_{H,L}}) = \rho_{\beta_0} \cdot e^{-x_{S_{Low,High}}}$$
$$\simeq \rho_{\beta_0} \cdot e^{-k_S \cdot u_a(t) \cdot u_p(t) \cdot u_{f_{Low,High}}}$$

The available evidence from the literature suggests that motor impairment shows a strong dependence on stimulation frequency. When this stimulation frequency is sufficiently high, DBS can effectively override the intrinsic pathological activity [Reference 9]. Thus, stimulation frequency is the key parameter that conditions the transition from a saturated to linear relationship in the beta band response to stimulation parameter. A chosen minimum frequency $u_{f_L}=70$ Hz is required in order to reduce the beta activity, whereas above the chosen maximum frequency $u_{f_H}=130$ Hz, a further reduction can be obtained only by increasing the stimulation amplitude and/or pulse-width.

The effect of disturbances will now be considered.

Above there is discussed the modelling of the main characteristics of the temporal evolution of the modulation of the beta band signal caused by the stimulation signal, which is essential a neurological effect at the target area of the brain from which measurements are taken. In addition, a set of other, as yet unmodelled phenomena may be taken into consideration and represented as modelling noise and disturbances. A succinct description of these disturbances is given for a sound completeness of the models proposed, although not essential.

Disturbances may be classified into two categories.

The first category comprises disturbances that are applied to the functional blocks of the modelling unit 30 described above. The first category includes a state disturbance v that is applied to the modulation dynamics block 33 and directly affects the temporal dynamics of the state variables of the dynamic evolution of the gross average of the beta band signal and state variable of the stimulation effect $x_E$. The first category also includes a saturation disturbance m that is applied to the modulation saturation block 34 and affects the generation of the saturated signal.

The second category of disturbances comprises external disturbances to the beta band signal. These are of particular importance in the field of DBS because they have the potential to cause significant distortions to the LFP measured from inside the target area. The external disturbance signal generator 36 mentioned above generates an external disturbance signal w representing external disturbances to the beta band signal of the this second category as will now be described in detail.

Figure 11:
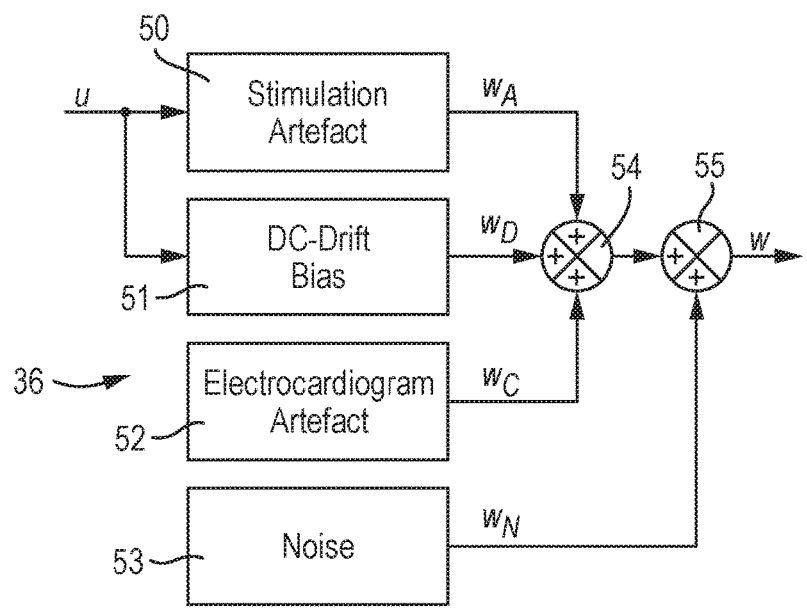
FIG. 11 is a functional block diagram of an external disturbance signal generator of the emulation apparatus.

As shown in FIG. 11, the external disturbance signal generator 36 includes four functional blocks that output respective signals representing different types of external disturbance, as follows.

The external disturbance signal generator 36 includes a stimulation artefact block 50 outputs a signal representing artefacts of the stimulation signal on the signal measured from the human or animal body. These are the main external disturbances and come from the stimulation pulses themselves. Such artefacts can in the worst case be a million times larger than the actual LFP signal recorded from the brain that is typically in the range of 1~10 μV. Such extremely low signal to noise ratio (SNR) is one of the most important barriers in processing meaningfully signals recorded from the brain whiles simultaneously applying high frequency electrical stimulations.

Figure 12:
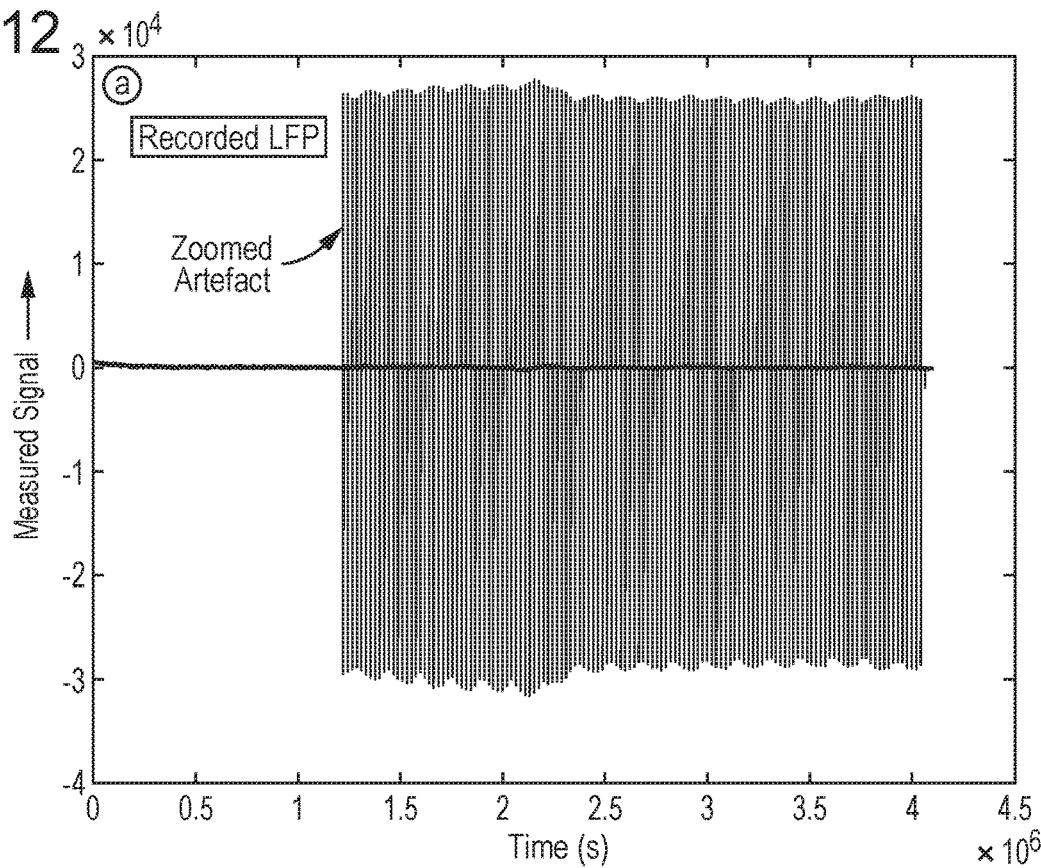
FIGS. 12 and 13 are graphs at different time scales of an example of an LFP signal on which a stimulation artefact is present.
Figure 13:
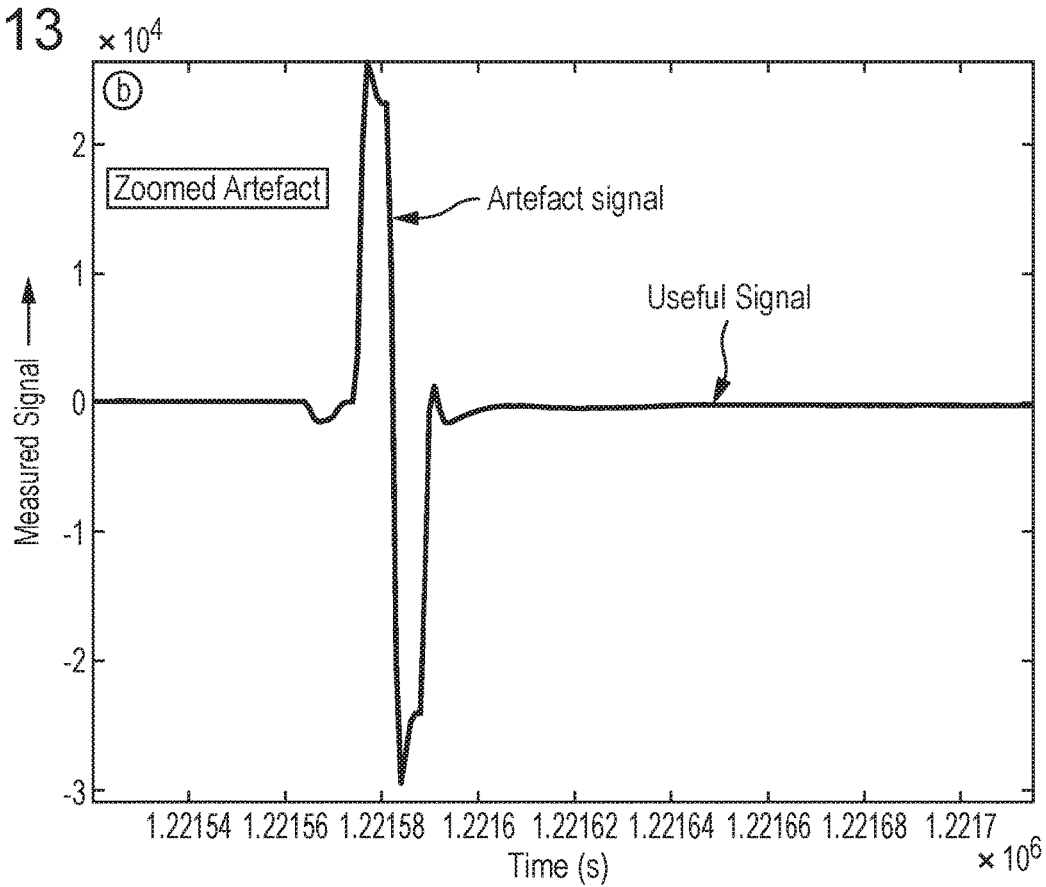

By way of example, FIGS. 12 and 13 both show the same example, at two different time scales, of a signal measured from the target area during simultaneous stimulation and recording from a PD patient with a DBS implant. As can be seen from FIG. 13 in particular, a single biphasic stimulation pulse is measured almost intact (although with reduced amplitude) despite high common mode rejection in the differential amplification of the recorded brain signal, and several stages of filtering. Such stimulation artefacts may in some circumstances lead to large aliasing effects.

Figure 14:
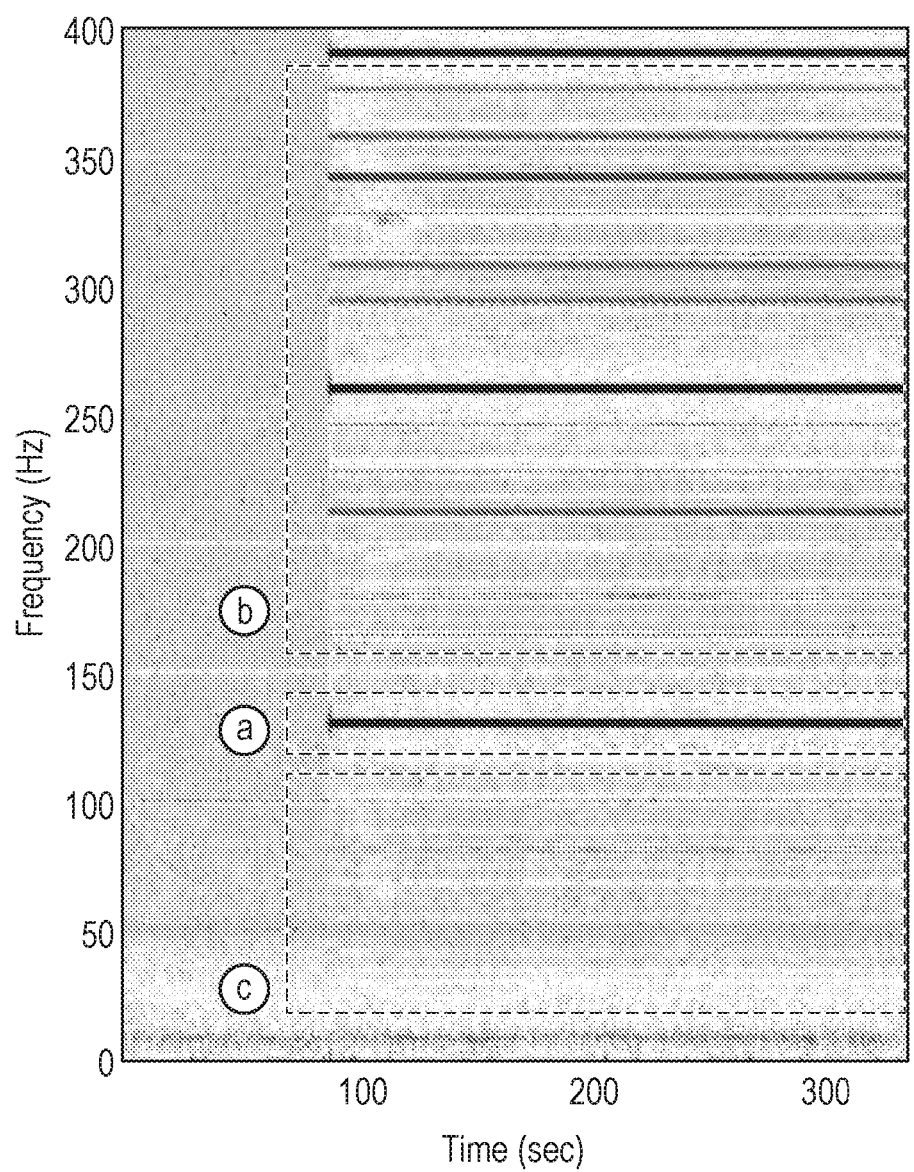
FIG. 14 is plot of the spectral intensity of an LFP signal on which a stimulation artefact is present.

An example of such aliasing effects can be seen for example in FIG. 14 illustrating actual data come from a simultaneous recording and stimulation where the amplitude $u_a$=3.5 V, pulse-with $u_p$=60 μs and frequency $u_f$=130 Hz. FIG. 14 shows that the impacts of stimulation artefacts are particularly deleterious and spread across a large frequency band for a stimulation amplitude $u_a$=3.0 V, pulse-with $u_p$=60 μs and frequency $u_f$=130 Hz. In particular, FIG. 14a shows the main harmonic 130 Hz harmonic as a dark strip. FIG. 14b shows the expected integer harmonics at 260 and 390 Hz also as dark strips, and large number of aliased harmonics as lighter strips. And in FIG. 14c, it is seen that that aliased harmonics are present inside the frequency of interest (0-100 Hz), and especially the beta band (15-30 Hz).

Although not the subject of this application, this type of artefact has let to numerous publications on models to represent it and methods to mitigate it. Nonetheless, the stimulation artefact block 50 outputs a signal representing these artefacts.

The external disturbance signal generator 36 includes a DC-drift bias block 51 outputs a signal representing the DC-drift bias. Such a DC-drift bias appears because of an excess of charge accumulation over time on the electrodes used to measure a signal from the target area and on tissue, due to electrode asymmetry and tissue properties. The DC bias can potentially lead to the destruction of both the electrodes and the tissue, and is an important issue to take into consideration. This issue is particularly present when passive charge balance is used, and even with active charge balance albeit to a lesser level. By way of example FIG. 14 of [Reference 13] shows an example of the complex temporal evolution of the DC-drift bias with offset regulation charge balancer, which seems to follow a second order under damp transfer function as the stimulation pulses are delivered. Because this DC-drift bias is several magnitudes larger than the signal of interest, it can lead to saturation and inadequate brain signal measurements.

The external disturbance signal generator 36 includes an electrocardiogram artefact block 52 that outputs a signal representing electrocardiogram artefacts.

The external disturbance signal generator 36 includes a noise block that outputs a signal representing noise, for example electronic components noise, (typically mains noise including 50/60 Hz harmonics) and electromagnetic interferences due to electrical radiation from external devices. Such different sources of noises add up together giving an elevated noise floor that may corrupt measurements.

A specific example of the model implemented by the functional blocks of the modelling unit 30 will now be given. This section defines the mathematical relationships representing the full standard model, which allows its numerical and electronic implementation, and forms the basis for the state-space representation of the 'nonlinear (Hammerstein-Wiener) stochastic time-varying differential-algebraic equation' modelling of how the beta reduction $\rho_\beta$ responds to the electrical stimulation parameters: amplitude $u_a$, pulse-with $u_p$ and frequency $u_f$ [Reference 2].

It is possible to express the transfer function between the state variable (output) $x_D$ representing the dynamic beta modulation and the stimulation 'pulse action' $u_{PA}$ representing here the input (and indeed the actual stimulation pulse u), when considering at this stage the modulation dynamics block 33 as a time-invariant system, by a second order lowpass system given by equation (24), which is re-written in the standard canonical form in equation (33) allowing the direct use of standard analysis results and derivation of the state-space model [Reference 9].

$$H_{ED}(s) = \frac{k_S \cdot \omega_\eta^2}{s^2 + 2 \cdot \xi \cdot \omega_\eta \cdot s + \omega_\eta^2} \tag{33}$$

with $k_S = k_E \cdot k_D$ $$\omega_\eta = \frac{1}{\sqrt{\tau_E \cdot \tau_D}} \quad \& \quad \xi = \frac{1}{2} \cdot \frac{\tau_E + \tau_D}{\sqrt{\tau_E \cdot \tau_D}}$$

In particular, from standard analysis [Reference 9], the equivalent time-varying ordinary differential equation expressed by equation (34) is derived directly, to which there is added a zero mean stationary stochastic process v(t) to represent measurement and modelling errors of the state, a time-varying time constant $\tau_D$ (t) and an overall time-varying static gain $k_S$(t) instead of constant as described above.

$$\ddot{x}_D(t) = -a_1(t) \cdot x_D(t) - a_2(t) \cdot \dot{x}_D(t) + b_1(t) \cdot u_{PA}(t) + v(t) \tag{34}$$

with $\dot{x}_D(t) = \frac{dx_D(t)}{dt}; \ddot{x}_D(t) = \frac{d^2 x_D(t)}{dt}$ $a_1(t) = \omega_\eta^2(t) = \frac{1}{\tau_E \cdot \tau_D(t)}$ $a_2(t) = 2 \cdot \xi(t) \cdot \omega_\eta(t) = \tau_E + \tau_D(t)$ $b_1(t) = k_S \cdot \omega_\eta^2(t) = \frac{k_S(t)}{\tau_E \cdot \tau_D(t)}$ The actual saturated modulation state $x_S$ due to stimulation parameters is limited by the Wiener memoryless (nonlinear) saturation function $f_W$ defined in equation (29), to which there is added a zero mean stationary stochastic process m(t) to represent also modelling errors of the actual saturated beta reduction factor as defined by equation (35).

$$x_s(t) = \hat{f}_W(t, x_D(t), u_a(t), u_p(t), u_f(t)) + m(t) \tag{35}$$

The static algebraic relationship $\rho_\beta$ allows to estimate the reduced beta magnitude $\hat{y}_{\beta_{LFP}}$ due to electrical stimulation using equation (15), to which there is added the external disturbances w composed of the stimulation artefact, electrocardiogram artefact and noise; this estimated reduced beta $\hat{y}_{\beta_{LFP}}$ is expressed by equation (36).

$$\hat{y}_{\beta_{LFP}}(t) = \rho_{\beta_0} \cdot e^{-x_S(t)} \cdot x_{\beta_{LFP}}(t) + w(t) \tag{36}$$

A mono-biomarker state-space model may be applied as follows.

In order to establish the our mono-biomarker state-space model (based on beta band—$\beta$—only), a change of variable is operated as per standard canonical transformation to re-write equation (34) of $x_D$ by equation (37) [Reference 9].

$$x_3(t) = x_D(t) \ \& \ x_4(t) = \dot{x}_D(t) \tag{37}$$

$$(a) \begin{cases} \dot{x}_3(t) = \dot{x}_D(t) \\ \quad = x_4(t) \end{cases}$$

$$(b) \begin{cases} \dot{x}_4(t) = \ddot{x}_D(t) \\ \quad = -a_1 \cdot x_3(t) - a_2 \cdot x_4(t) + b_1 \cdot u_{PA}(t) \end{cases}$$

The exact same principle is followed to re-write equation (24) of $x_{D_{High}}$ and $x_{D_{Low}}$ by equation (38).

$$x_1(t) = x_{D_{High}}(t) \ \& \ x_2(t) = \dot{x}_{D_{High}}(t) \tag{38}$$

$$(a) \begin{cases} \dot{x}_1(t) = \dot{x}_{D_{High}}(t) \\ \quad = x_2(t) \end{cases}$$

$$(b) \begin{cases} \dot{x}_2(t) = \ddot{x}_{D_{High}}(t) \\ \quad = -a_1 \cdot x_1(t) - a_2 \cdot x_2(t) + b_1 \cdot u_{PA_{High}}(t) \end{cases}$$

Rewriting $x_{D_{Low}}$ from equation (24) provides equation (39).

$$x_5(t) = x_{D_{Low}}(t) \ \& \ x_6(t) = \dot{x}_{D_{Low}}(t) \tag{39}$$

$$(a) \begin{cases} \dot{x}_5(t) = \dot{x}_{D_{Low}}(t) \\ \quad = x_6(t) \end{cases}$$

$$(b) \begin{cases} \dot{x}_6(t) = \ddot{x}_{D_{Low}}(t) \\ \quad = -a_1 \cdot x_5(t) - a_2 \cdot x_6(t) + b_1 \cdot u_{PA_{Low}}(t) \end{cases}$$

The mono-biomarker continuous-time 'nonlinear (Hammerstein-Wiener) stochastic time-varying differential-algebraic state-space equation' (see below for the demonstration of its differential-algebraic nature) is given by equation (40), where a lowercase letter represent a unidimensional variable, uppercase for a vector and bold uppercase for a matrix.

$$U(t) = \hat{f}_H(t, u_{Na}(t), u_{Np}(t), u_{Nf}(t)) \tag{40}$$

$$= [u_a, u_p, u_f]^T$$

-continued $$U_{PA}(t) = f_{PA}(t, U(t), u_{f_{High}}, u_{f_{Low}})$$

$$\dot{X}(t) = A(t) \cdot X(t) + B(t) \cdot U_{PA}(t) + F \cdot V(t)$$

$$Y(t) = C \cdot X(t)$$

$$x_S(t) = \hat{f}_W(t, Y(t)) + m(t)$$

$$\hat{y}_{\beta_{LFP}}(t) = \rho_{\beta_0} \cdot e^{-x_S(t)} \cdot x_{\beta_{LFP}}(t) + w(t)$$

From equation (40), U represents the limited stimulation pulse (here expressed as a vector) to a safe clinical range of the original neuromodulation pulse parameters $u_{Na,p,f}$ as defined by equation (28). $U_{PA}$ is the 'pulse action' vector defined by equation (41) based on equations (20) and (30).

$$U_{PA}(t) = \begin{bmatrix} u_{PA_{High}}(t) \\ u_{PA}(t) \\ u_{PA_{Low}}(t) \end{bmatrix} = f_{PA}(t, U(t), u_{f_{High}}, u_{f_{Low}}) \tag{41}$$

$$= \begin{bmatrix} u_{f_{High}} \\ u_f(t) \\ u_{f_{Low}} \end{bmatrix} \cdot [u_a(t) \ u_p(t)] \cdot \begin{bmatrix} 0 & 0 \\ 1 & 0 \end{bmatrix} \cdot \begin{bmatrix} u_a(t) \\ u_p(t) \end{bmatrix}$$

$$= \begin{bmatrix} u_a(t) \cdot u_p(t) \cdot u_{f_{High}} \\ u_a(t) \cdot u_p(t) \cdot u_f(t) \\ u_a(t) \cdot u_p(t) \cdot u_{f_{Low}} \end{bmatrix}$$

X is the state vector, $\dot{X}$ is the derivative of the state vector defined by equation (42) based on equations (37), (38) and (39). In equation (42), the vector V is a zero mean stationary stochastic process, whereas Y is the output vector.

$$X(t) = [x_1(t) \ x_2(t) \ x_3(t) \ x_4(t) \ x_5(t) \ x_6(t)]^T \tag{42}$$

$$= [x_{D_{High}}(t) \ \dot{x}_{D_{High}}(t) \ x_D(t) \ \dot{x}_D(t) \ x_{D_{Low}} \ \dot{x}_{D_{Low}}(t)]^T$$

$$V(t) = [v_{High}(t) \ v(t) \ v_{Low}(t)]^T$$

$$Y(t) = [x_1(t) \ x_3(t) \ x_5(t)]^T$$

$$= [x_{D_{High}}(t) \ x_D(t) \ x_{D_{Low}}(t)]^T$$

From equation (40), A is the state matrix, B is the input matrix, F is the state measurement and modelling error matrix, C is the output matrix and y the scalar output. These matrices are defined in equation (43).

Finally, from equation (40), the saturated modulation state $x_S$ is defined by equations (29), (30), (32) and (35); whereas the estimated reduced beta band $\hat{y}_{\beta_{LFP}}$ is defined by equations (15) and (36).

$$A(t) = \begin{bmatrix} 0 & 1 & 0 & 0 & 0 & 0 \\ -a_1(t) & -a_2(t) & 0 & 0 & 0 & 0 \\ 0 & 0 & 0 & 1 & 0 & 0 \\ 0 & 0 & -a_1(t) & -a_2(t) & 0 & 0 \\ 0 & 0 & 0 & 0 & 0 & 1 \\ 0 & 0 & 0 & 0 & -a_1(t) & -a_2(t) \end{bmatrix} \tag{43}$$

-continued $$B(t) = \begin{bmatrix} 0 & 0 & 0 \\ b_1(t) & 0 & 0 \\ 0 & 0 & 0 \\ 0 & b_1(t) & 0 \\ 0 & 0 & 0 \\ 0 & 0 & b_1(t) \end{bmatrix} \& F = \begin{bmatrix} 0 & 0 & 0 \\ 1 & 0 & 0 \\ 0 & 0 & 0 \\ 0 & 1 & 0 \\ 0 & 0 & 0 \\ 0 & 0 & 1 \end{bmatrix}$$

$$C = \begin{bmatrix} 1 & 0 & 0 & 0 & 0 & 0 \\ 0 & 0 & 1 & 0 & 0 & 0 \\ 0 & 0 & 0 & 0 & 1 & 0 \end{bmatrix}$$

The model given in equation (40) is based on a single biomarker; here the beta band β, but defined with two variables: the dynamic evolution $x_D$ of the beta envelop and its derivative $\dot{x}_D$.

As an important note, Wills et al. have proposed an approach to identify automatically and online Hammerstein-Wiener state-space models [Reference 2]. This approach could be used with the model in order to update automatically its time-varying parameters, as well as individualised it to a particular person. Also, data presented by Qian et al. [Reference 3] used for deriving the steady-state behaviour of our model is limited to a narrow region of the complex nonlinear space of the beta response to stimulation as suggested by the mean field model of the basal ganglia-thalamocortical system (BGTCS); this model has a structure and parameters based on physiology and anatomy, and has been shown to account for some electrophysiological correlates of Parkinson's disease (PD) [Reference 10], [Reference 11]. It is expected that the time-varying static gain $k_S(t)$ to be dependent not only on the time variable, but also on the stimulation parameters: $k_S(t)=f_S(t,u_a(t),u_p(t),u_f(t))$. In this way, it would possible to replicate nonlinear and time dependent behaviours of beta response to stimulation as studied by Grado et al. [Reference 12]. Thus, our proposed model is a global and steady-state approximation of the complex nonlinear behaviour of beta response to stimulation, that can be easily adapted by setting the adequate time constant $\tau_D(t)$ and static gain $k_S(t)$ to the region of interest.

In order to establish the structure of the model (ordinary differential equation (ODE) vs. differential-algebraic equation (DAE), it is evaluated if the determinant of its Jacobian matrix is singular (non-invertible) leading to a differential-algebraic equation (DAE), or non-singular (invertible) leading to an ordinary differential equation (ODE). To express the Jacobian matrix, the situation is considered when the system is not saturated (in the linear region of both Hammerstein and Weiner saturation functions $\hat{f}_H$ and $\hat{f}_W$ respectively) with no disturbances; therefore when $x_S=x_D=z_1$, $\dot{x}_D=z_2$ and $v=m=w=0$. Equations (36) and (37) are combined to set the non-saturated system of equations (44). A change of variable from x to z is done in order to avoid confusion.

$$F_1 = \dot{z}_1(t) - z_2(t) = 0$$

$$F_2 = a_1 \cdot z_1(t) \pm \dot{z}_2(t) + a_2 \cdot z_2(t) - b_1 \cdot u_{PA}(t) = 0$$

$$F_3 = -\rho_{\beta_0} \cdot e^{-zi(t)} \cdot x_{\beta_{LFP}}(t) + z_3(t) = 0 \quad (44)$$

Setting the state vector $Z=[z_1 \ z_2 \ z_3]^T$, the system from equation (44) can be re-written on its matrix form in equation (45).

$$F(t, Z(t), \dot{Z}(t)) = \begin{bmatrix} F_1(t, Z(t), \dot{Z}(t)) \\ F_2(t, Z(t), \dot{Z}(t)) \\ F_3(t, Z(t), \dot{Z}(t)) \end{bmatrix} = 0 \quad (45)$$

The determinant of the Jacobian matrix $|\partial F/\partial \dot{Z}|$ of the system $F(t, z(t), \dot{Z}(t))$ given by equation (46) is singular (non-invertible), leading therefore to conclude that our model has the structure of a differential-algebraic equation (DAE).

$$\left| \frac{\partial F}{\partial \dot{Z}} \right| = \begin{vmatrix} \frac{\partial F_1}{\partial \dot{z}_1} & \frac{\partial F_1}{\partial \dot{z}_2} & \frac{\partial F_1}{\partial \dot{z}_3} \\ \frac{\partial F_2}{\partial \dot{z}_1} & \frac{\partial F_3}{\partial \dot{z}_2} & \frac{\partial F_3}{\partial \dot{z}_3} \\ \frac{\partial F_3}{\partial \dot{z}_1} & \frac{\partial F_3}{\partial \dot{z}_2} & \frac{\partial F_3}{\partial \dot{z}_3} \end{vmatrix} = \begin{vmatrix} 1 & 0 & 0 \\ 0 & 1 & 0 \\ 0 & 0 & 0 \end{vmatrix} = 0 \quad (46)$$

A multi-biomarker state-space model may be used as follows.

Finally, the model given by the state-space equation (40) can be easily extend by adding additional biomarkers of Parkinson's disease (PD). In order to exemplify this, let us consider that three biomarkers of PD have been retained: the beta band noted with the index β and defined by the state variable $X_\beta$, a putative biomarker Δ (which could be for example the alpha band, gamma band, or a combination of frequency bands) defined by the state variable $x_\lambda$, and the tremor T measured by an accelerometer attached to the subject's wrist defined by the state variable $X_T$. Supposing that all three biomarkers respond on their own way to the same stimulation command U, and are not coupled to each other (i.e. do not interact with each other). In this case, the multi-biomarker continuous-time 'nonlinear (Hammerstein-Wiener) stochastic time-varying differential-algebraic state-space model in equation (47) is given by the same structure of the equation (40), but extended to take into consideration the new biomarkers $X_\lambda$ and $X_T$.

$$\begin{cases} U(t) = \hat{f}_H(t, u_{Na}(t), u_{Np}(t), u_{Nf}(t)) \\ U_{PA}(t) = f_{PA}(t, U(t), u_{f_{High}}, u_{f_{Low}}) \end{cases} \quad (47)$$

② $\begin{cases} \dot{X}_\beta(t) = A_\beta(t) \cdot X_\beta(t) + B_\beta(t) \cdot U_{PA}(t) + F_\beta \cdot V_\beta(t) \\ \dot{X}_\lambda(t) = A_\lambda(t) \cdot X_\lambda(t) + B_\lambda(t) \cdot U_{PA}(t) + F_\lambda \cdot V_\lambda(t) \\ \dot{X}_T(t) = A_T(t) \cdot X_T(t) + B_T(t) \cdot U_{PA}(t) + F_T \cdot V_T(t) \end{cases}$ ③ $\begin{cases} Y_\beta(t) = C_\beta \cdot X_\beta(t) \\ Y_\lambda(t) = C_\lambda \cdot X_\lambda(t) \\ Y_T(t) = C_T \cdot X_T(t) \\ Y_C(t) = [Y_\beta(t) \ Y_\lambda(t) \ Y_T(t)]^T \end{cases}$ ④ $X_S(t) = \hat{F}_W(t, Y_C(t)) + P \cdot M(t)$ ⑤ $\hat{Y}(t) = F_A(t, X_S(t)) \cdot X_A(t) + Q \cdot W(t)$ From equation (47), the first relation ① defines the command variables. U is the limited stimulation pulse parameter vector derived from the original neuromodulation pulse parameters $u_{Na,p,f}$ as defined by equation (28). $U_{PA}$ is the 'pulse action' vector defined by equation (41). For the same reason as already mentioned above, for the efficient implementation of this model for numerical simulation, it is completely equivalent in term of steady-state behaviour to use the exact stimulation pulses as generated by an actual neurostimulator, or to use the 'pulse action' $U_{PA}$ shown in equation (41). The advantage of using this 'pulse action' $U_{PA}$ rather than the actual stimulation pulse is that the simulation will be much faster.

The second relation ②︎ from equation (47) defines the multivariable state-space equation here represented as three sub-set of equations for more clarity; they can be indeed grouped into a single expression by simply concatenating them vertically. $X_{\beta,\lambda,T}$ are the state vectors of the three states variables considered in this case: the beta band, the putative biomarker $\lambda$, and the tremor T respectively; $\dot{X}_{\beta,\lambda,T}$ are their respective derivatives, and both are defined by equation (48). Matrices $A_{\beta,\lambda,T}$ the state matrices, have exactly the same structure as the matrix A given by equation (43), where $a_1$ and $a_2$ are replaced by their equivalent variables: $a_1 \rightarrow a_{\beta,\lambda,T_1}$ and $a_2 \rightarrow a_{\beta,\lambda,T_2}$. Similarly, matrices $B_{\beta,\lambda,T}$ the input matrices, are each defined exactly as the matrix B given by equation (43), and operating the same variable renaming as per above: $b_1 \rightarrow b_{\beta,\lambda,T_1}$. Whereas, matrices $F_{\beta,\lambda,T}$, the state measurement and modelling error matrices, are each defined exactly as the matrix F given by equation (43): $F_{\beta,\lambda,T} = F$.

$$X_{\beta,\lambda,T}(t) = \begin{bmatrix} x_{\beta,\lambda,T_1}(t) & x_{\beta,\lambda,T_2}(t) & x_{\beta,\lambda,T_3}(t) \\ x_{\beta,\lambda,T_4}(t) & x_{\beta,\lambda,T_5}(t) & x_{\beta,\lambda,T_6}(t) \end{bmatrix}^T = \begin{bmatrix} x_{\beta,\lambda,T_{D_{High}}}(t) & \dot{x}_{\beta,\lambda,T_{D_{High}}}(t) & x_{\beta,\lambda,T_D}(t) \\ x_{\beta,\lambda,T_D}(t) & x_{\beta,\lambda,T_{D_{Low}}}(t) & x_{\beta,\lambda,T_{Low}}(t) \end{bmatrix}^T \quad (48)$$

$$V_{\beta,\lambda,T}(t) = [v_{\beta,\lambda,T_{High}}(t) \quad v_{\beta,\lambda,T}(t) \quad v_{\beta,\lambda,T_{Low}}(t)]^T$$

Vectors $V_{\beta,\lambda,T}$ are zero-mean stationary stochastic processes to represent state measurement and modelling errors.

The third relation ③︎ from equation (47) represents the multivariable output equation, where $Y_{\beta,\lambda,T}$ are the output vectors defined by equation (49). Matrices $C_{\beta,\lambda,T}$, the output matrices, are each defined exactly as the matrix C given by equation (43):

$$C_{\beta,\lambda,T} = C. \quad (49)$$

$$Y_{\beta,\lambda,T}(t) = [x_{\beta,\lambda,T_1}(t) \quad x_{\beta,\lambda,T_3}(t) \quad x_{\beta,\lambda,T_5}(t)]^T = [x_{\beta,\lambda,T_{D_{High}}}(t) \quad x_{\beta,\lambda,T_D}(t) \quad x_{\beta,\lambda,T_{D_{Low}}}(t)]^T$$

From equation (47), the fourth relation ④︎ is the multivariable dynamic Wiener saturation relationships which are defined by equation (50), where $X_S$ is the saturated state dynamics vector, $\hat{F}_W$ is the dynamic Wiener saturation vector, P and M are respectively the modelling errors of the actual saturated state dynamics matrix and vector.

$$④︎ \quad X_S(t) = \hat{F}_W(t, Y_C(t)) + P \cdot M(t) \quad (50)$$

with

-continued $$X_S(t) = \begin{bmatrix} x_{S_\beta}(t) \\ x_{S_\lambda}(t) \\ x_{S_T}(t) \end{bmatrix} \& F_W(t, .) = \begin{bmatrix} \hat{f}_{W_\beta}(t, Y_\beta(t)) \\ \hat{f}_{W_\lambda}(t, Y_\lambda(t)) \\ \hat{f}_{W_T}(t, Y_T(t)) \end{bmatrix}$$

$$P = \begin{bmatrix} 1 & 0 & 0 \\ 0 & 1 & 0 \\ 0 & 0 & 1 \end{bmatrix} \& M(t) = \begin{bmatrix} m_\beta(t) \\ m_\lambda(t) \\ m_T(t) \end{bmatrix}$$

Finally, from equation (47) the fifth relation ⑤︎ is the static algebraic equation, where $\hat{Y}$ is the estimated output vector, $F_A$ is the algebraic function matrix, $X_S$ is the saturated dynamic state vector, $X_A$ is the algebraic input vector, Q and W are respectively the external disturbance matrix and vector. Those vectors and matrices are defined by equation (51).

$$⑤︎ \quad \hat{Y}(t) = F_A(t, X_S(t)) \cdot X_A(t) + Q \cdot W(t) \quad (51)$$

with $$\hat{Y}(t) = \begin{bmatrix} \hat{y}_{\beta_{LFP}}(t) \\ \hat{y}_{\lambda_{LFP}}(t) \\ \hat{y}_T(t) \end{bmatrix} \& X_A(t) = \begin{bmatrix} x_{\beta_{LFP}}(t) \\ x_{\lambda_{LFP}}(t) \\ x_T(t) \end{bmatrix}$$

$$F_A(t, .) = \begin{bmatrix} f_{A_\beta}(t, x_{S_\beta}(t)) & 0 & 0 \\ 0 & f_{A_\lambda}(t, x_{S_\lambda}(t)) & 0 \\ 0 & 0 & f_{A_T}(t, x_{S_T}(t)) \end{bmatrix}$$

$$Q = \begin{bmatrix} 1 & 0 & 0 \\ 0 & 1 & 0 \\ 0 & 0 & 1 \end{bmatrix} \& W(t) = \begin{bmatrix} w_\beta(t) \\ W_\lambda(t) \\ w_T(t) \end{bmatrix}$$

In equation (51), $f_{A_{\beta,\lambda,T}}$ are the actual algebraic function used for predicting each of the estimated state variable, and are defined in equation (52).

$$\begin{cases} f_{A_\beta}(t, x_{S_\beta}(t)) = \rho_{\beta_0} \cdot e^{-x_{S_\beta}(t)} \cdot x_\beta(t) \\ f_{A_\lambda}(t, x_{S_\lambda}(t)) = \rho_{\lambda_0} \cdot e^{-x_{S_\lambda}(t)} \cdot x_\lambda(t) \\ f_{A_T}(t, x_{S_T}(t)) = \rho_{T_0} \cdot e^{-x_{T_\lambda}(t)} \cdot x_T(t) \end{cases} \quad (52)$$

It should be highlighted here that the state-space model is not unique and depends on particular choices related to the modelling goals. As already mentioned, in the following definition, it is also considered that the three biomarkers beta $\beta$, the putative second biomarker $\Delta$ and the tremor T are decoupled from each other; i.e. they do not interact. This does not have to be the case, and in the situation of coupled biomarkers our multivariable model structure applies as it, and one has only to adapt the actual definition of the vectors and matrices used accordingly.

Finally, by applying classical continuous-time to discrete-time transformation, there is obtained the discrete-time equivalent of the continuous-time mono- or multi-biomarker 'nonlinear (Hammerstein-Wiener) stochastic time-varying differential-algebraic state-space model' given respectively in equations (40) and (47). It is indeed these discrete-time expressions that are actually implemented in a software implementation, as discussed further below.

The emulation apparatus 1 may in general be implemented entirely in software, entirely in hardware or in a combination thereof by implementing different functional blocks in hardware or software. Some key aspects to facilitate the implementation of the software and hardware emulation are highlighted as follows.

For a software implementation, the emulation apparatus 1 may be implemented by a computer program capable of execution by a computer apparatus. The computer program is configured so that, on execution, it causes the computer apparatus to operate as the emulation apparatus 1 and perform the emulation method. In this case, the emulation apparatus 1 processes digital signals representing the various signals mentioned above.

The computer apparatus, where used, may be any type of computer system but is typically of conventional construction. The computer program may be written in any suitable programming language. The computer program may be stored on a computer-readable storage medium, which may be of any type, for example: a recording medium which is insertable into a drive of the computing system and which may store information magnetically, optically or opto-magnetically; a fixed recording medium of the computer system such as a hard drive; or a computer memory.

In one convenient implementation, the emulation apparatus 1 may be implemented by a computer program in a simulation environment such as Matlab/Simulink.

In general, the practical realisation of the emulation apparatus 1 in software is straightforward merely by implementing the different function blocks described above by corresponding software blocks. Some optional details are as follows.

The implementation of the prior signal generator 10 can be done in two different ways. First, one can generate the prior signal as synthetic data that represent some aspects of current understanding of the LFP characteristics. In such a case, this function generates the synthetic envelope of the beta band activity either as the envelope of the power of the beta activity together with a carrier represented by a sinewave or a sum of sinewaves used to represent the beta band. This carrier will be then temporally multiplied by the modulated envelope (modulated by the stimulation command) in the modulation algebraic function.

An alternative solution is to use data directly recorded from an actual patient (i.e. a person with Parkinson's disease) when the stimulation is OFF. After adequate filtering and processing of the beta power envelope, the data can be used as the signal that will be modulated by the stimulation.

In addition, both the synthetic and actual participant data can be also directly defined at the temporal/voltage domain as opposed to the frequency/power domain as described above. Depending on the choice of the temporal vs. frequency domain, the correct set of parameters needs to be used as described above.

Turning to the modelling unit 30, the command saturation block 31 may be implemented by a classical saturation function.

The stimulation effect block 32 may be implemented by a first order system. From equation (33), a simple approach is to set $k_D=1$, leading to express $k_E$ by equation (53).

$$k_D=1 \Rightarrow k_E=k_S \quad (53)$$

Since the numerical value of $k_S$ is different depending on the domain (frequency vs. temporal) of the LFP provided by the LFP Generator function, $k_E$ can be seen as a variable parameter with regard to the domain of functioning (frequency vs. temporal).

Figure 15:
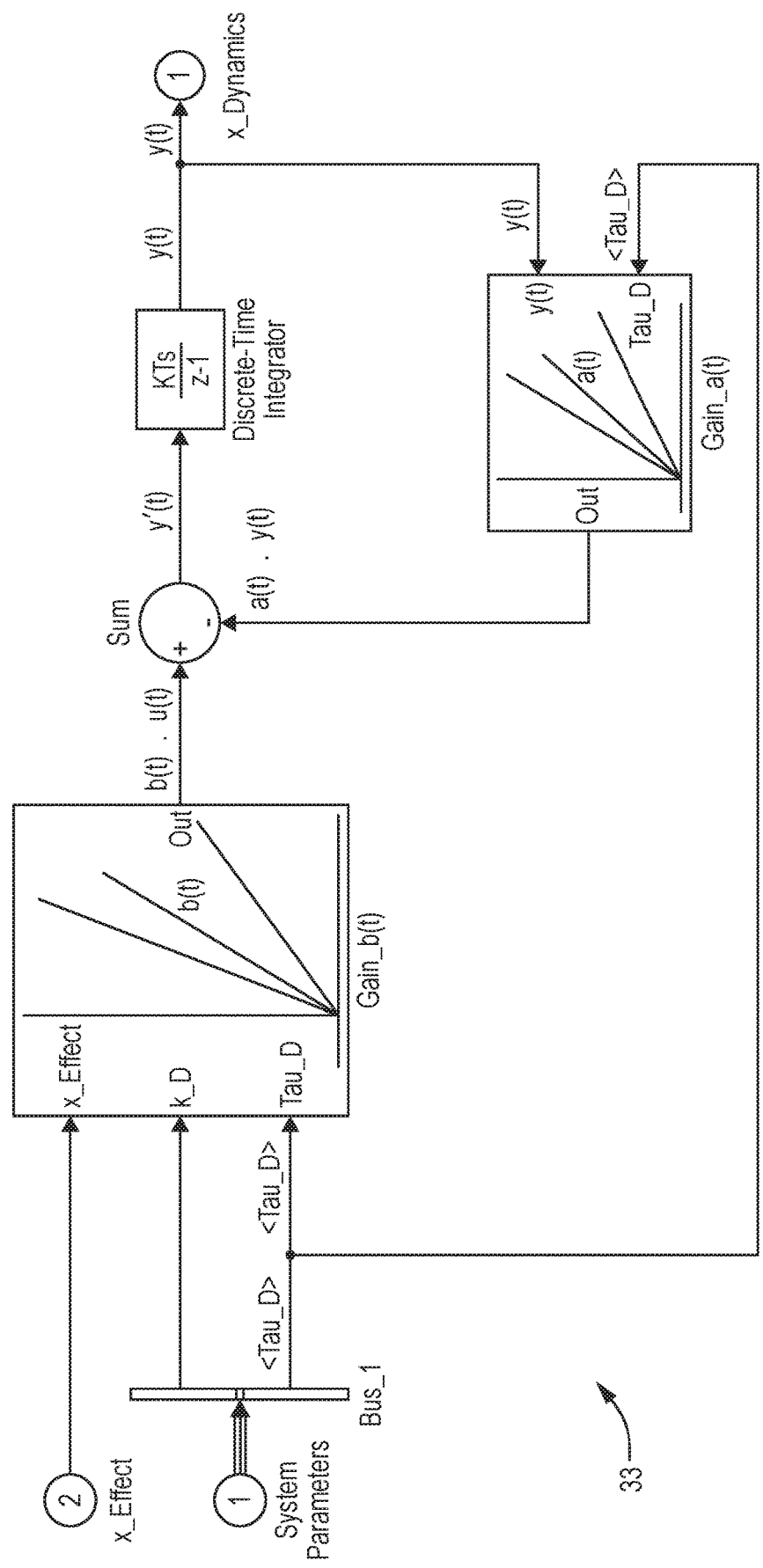
FIG. 15 is a graphical representation of an implementation in a simulation environment of a modulation dynamics block of a modelling unit of the emulation apparatus.

The modulation dynamics block 33 may be represented in its temporal or recurrent form for digital implementation. As mentioned above, since the modulation dynamics function is a time-variant first order system given by equation (27), it cannot be represented by a classical Laplace transfer function. An example of such implementation under Matlab/Simulink is presented in FIG. 15. In such case, there is a need to choose the right method of integration implemented by the discrete-time integrator. For instance, under Matlab/Simulink with a fixed-step discrete solver (no continuous state), the forward Euler integration method could be chosen to avoid algebraic loop during the initialisation stage. Alternatively, one can decide to consider a stationary model for a given period where the model parameters are seen as constant; thus, allowing the modulation block to be implemented by classical Laplace transform transfer function.

The modulation saturation block 34 may be implemented by a dynamic saturation function.

The modulation algebraic block 35 may be implemented directly by equation (15).

Figure 16:
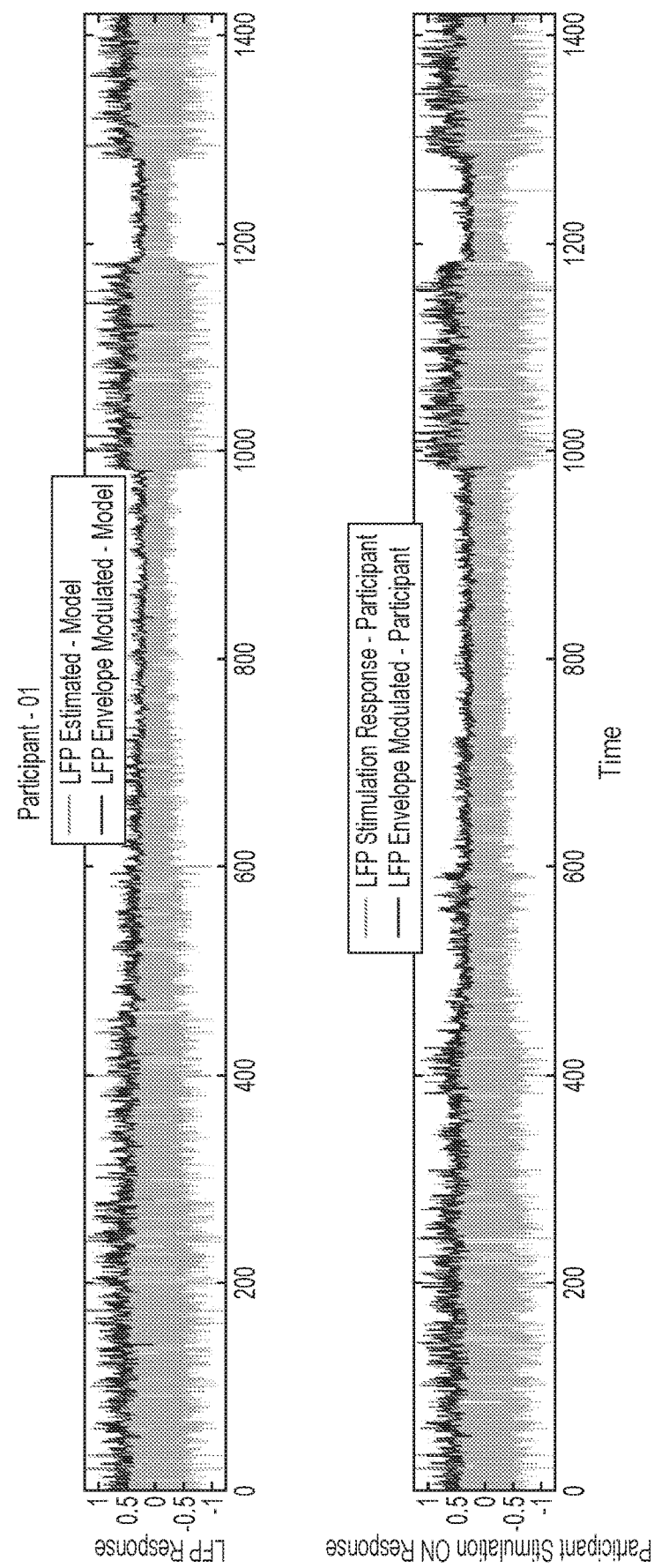
FIG. 16 is a set of graphs of signals recorded within an example of a software implementation of the emulation apparatus.
Figure 16:
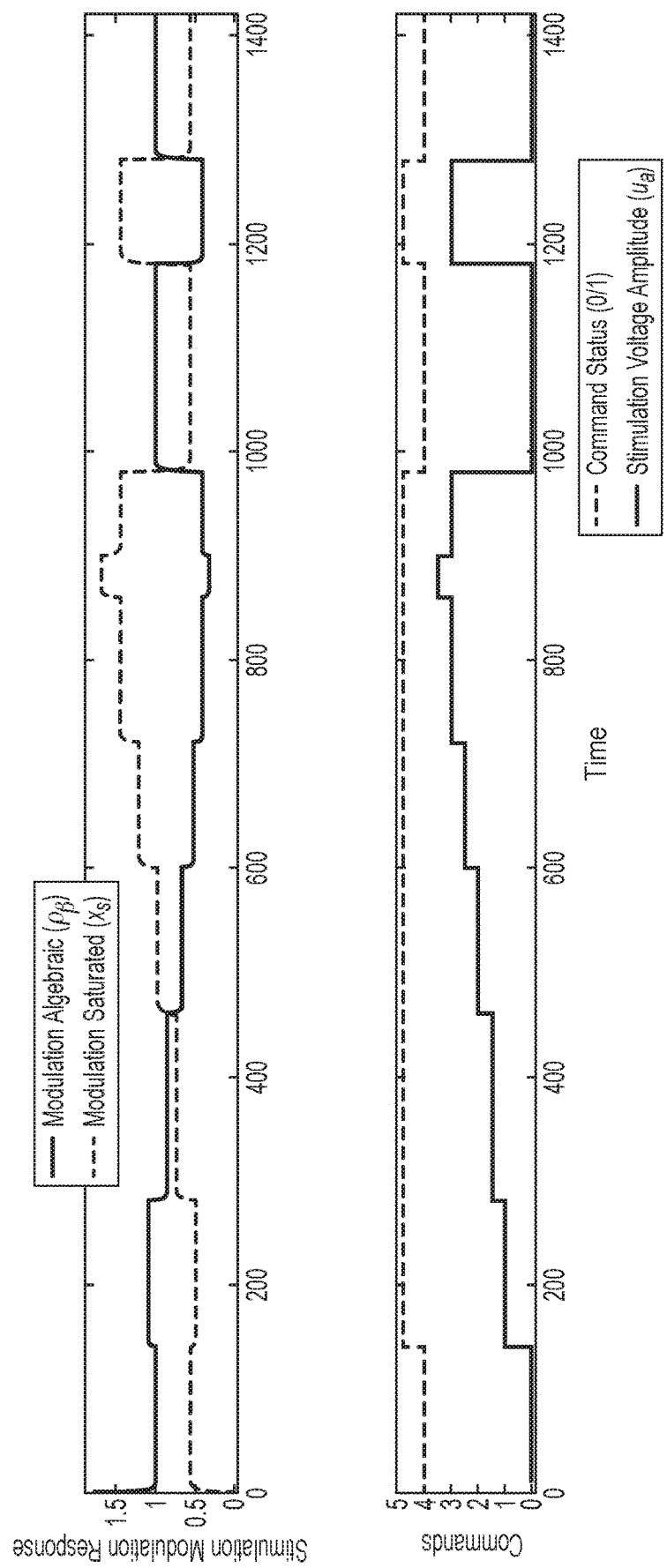

FIG. 16 shows an example of signals developed within a software implementation of the emulation apparatus. This example uses data from the actual participant between 0 and 114 seconds when the stimulation is OFF, which are repeated until the end of the simulation at 1420 seconds. The top plot shows the estimated beta power LFP response to stimulation $\hat{y}_{\beta_{LFP}}$, whiles the second plot (from top) shows the actual beta power response $y_{\delta_{LFP}}$ recorded from the participant. The third plot shows the saturated modulation $x_S$ and the modulation algebraic $\rho_{\beta_P}$ calculated by the model. The fourth plot shows when the stimulation is ON or OFF together with the actual stimulation amplitude $u_a$ applied to the participant brain. For modelling, the signal is the same.

For a hardware implementation, the emulation apparatus 1 may be implemented using standard electronic components, for example as follows.

The emulation apparatus 1 may be implemented either in an analogue, digital or mixed-design fashion. In the following example, an analogue implementation is described, but could be combined with the software implementation of any of the functional blocks as described above if a mixed-design approach is chosen. In that case, typically a supervisory computer will control the emulator, although this is not required, while a processor is used to implement the digital parts.

The prior signal generator 10 can use directly either the synthetic or actual participant data signal produced by the software implementation. Another possibility for the prior signal generator 10 to be implemented by an external signal generator, or an arbitrary wave generator (AWG) or another computer with a digital-to-analogue converter if it is desired to totally desynchronise the hardware emulation apparatus from the supervising computer. The latter option guarantees a complete desynchronisation between the LFP generator and the hardware emulation apparatus 1. Such a situation can be important if the hardware emulation apparatus 1 is used in closed-loop fashion to implement and test new advanced control algorithm for managing the symptoms of PD.

Turning to the modelling unit 30, the test signal is typically a temporal signal generated by the test signal generator 21, which may be part of an external neurostimulation device under test.

The command saturation block 31 may be implemented by a clamp operational amplifier or by a saturation circuit which operates to limit the voltage amplitude of the stimulation pulse. Limiting the pulse-width and frequency is a more complex task that is best performed at the supervisory computer level, or at the level of the external neurostimulation device, if it is used.

An alternative situation where the test signal represents parameters representing the waveform of the stimulation signal is for the command saturation block 31 to be implemented as a neurostimulation device which generates temporal stimulation signal in accordance with the supplied parameters, in which case the limitation function may be implemented by control of the supplied parameters prior to generation of the temporal signal.

Figure 17:
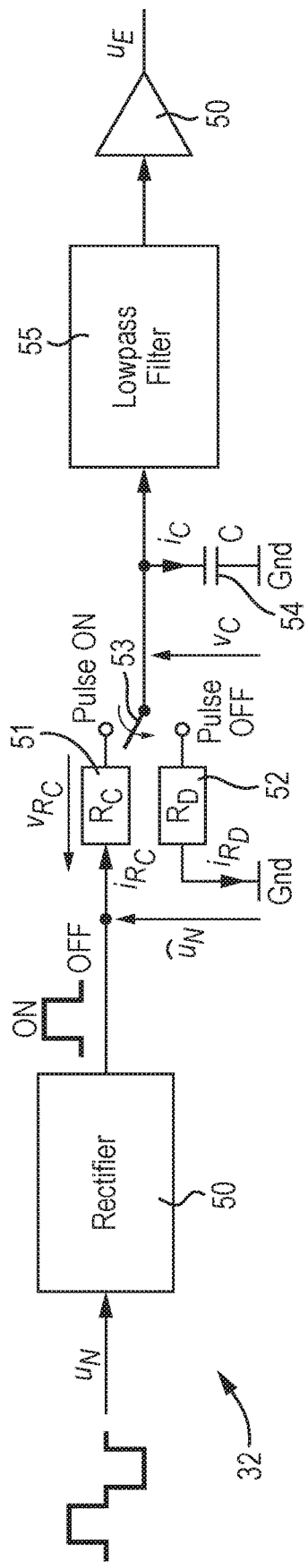
FIG. 17 is a functional block diagram of an implementation in hardware of a stimulation effect block of a modelling unit of the emulation apparatus.

The stimulation effect block 32 may be implemented by a circuit of the type shown in FIG. 17 and arranged as follows.

The first stage of the stimulation effect block 32 is a rectifier 50 which can be either a classical half-wave rectifier if the negative pulse is considered not to be physiologically meaningful, but simply for charge balance at the neural level, or otherwise by a full-wave rectifier.

The next stage of the stimulation effect block 32 comprises first and second resistors 51 and 52 and a switch 53 which implement equation (20) of the 'pulse action' $u_{PA}$ noting the very small duty cycle ($T_{ON}/T_{ON}$=0.0078) of the standard stimulation pulse (60 µs at 130 Hz). The first resistor 51 is connected to the output from the rectifier 50 while the second resistor 52 is connected to ground. The switch 53 switches synchronously with the stimulation pulses 3, connecting to the first resistor 51 when the pulse is on and to the second resistor 52 when the pulse is off. This approximates $u_{PA}$ at the pulse level, which is required especially when one desires to drive the hardware emulation apparatus 1 by an external third-party neurostimulation device as the test signal generator 21. The output of the switch 53 is connected to a capacitor 54 which is connected to ground and is therefore charged through the first resistor 51 when the stimulation pulse is ON, and discharged through the second resistor 52 when the stimulation pulse is OFF.

Figure 18:
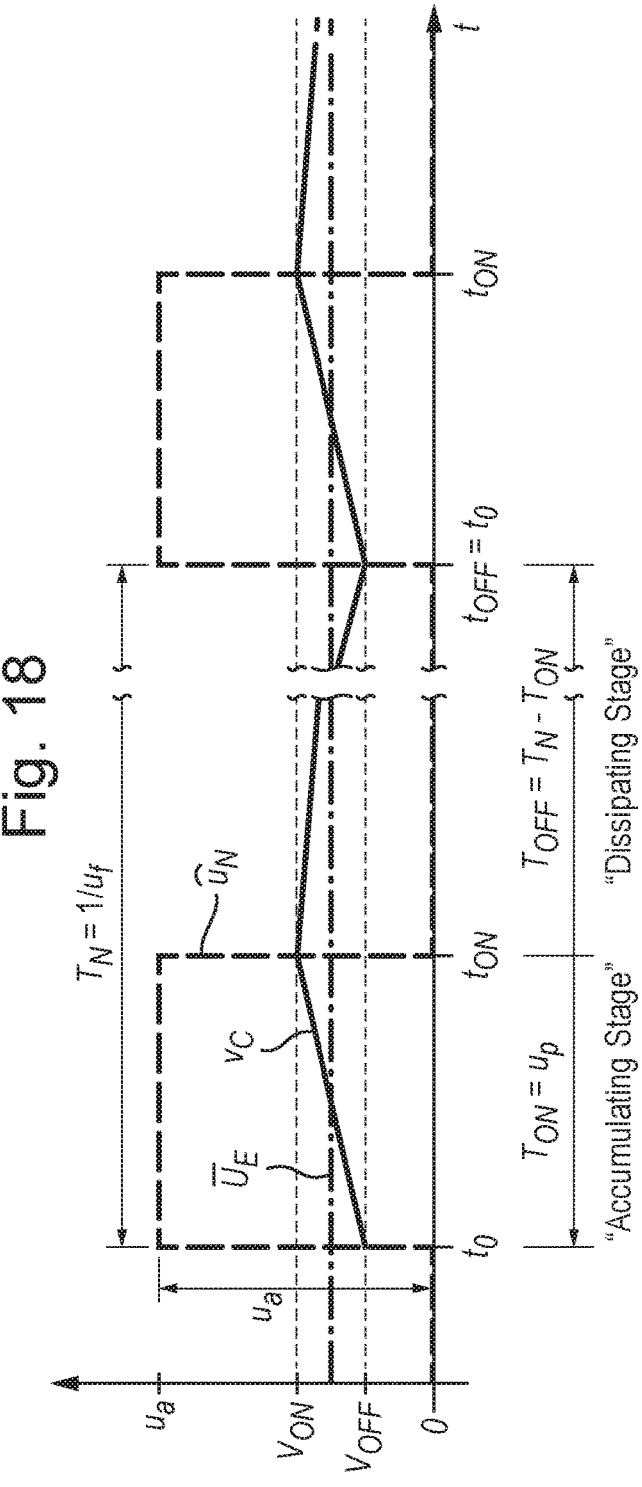
FIG. 18 is a chronogram of the operation of the stimulation effect block of FIG. 21.

By choosing the resistance $R_C$ of the first capacitor 51 and resistance $R_D$ of the second capacitor 52 such that $R_D \gg R_C$, the brief charge acquired when the stimulation is ON (typically 60 µs) is 'preserved' to a certain level when the stimulation is OFF (typically around 7.6 ms for a stimulation frequency of 130 Hz). This avoids the capacitor C discharging too much or completely when the pulse is OFF, which in turn generates a more stable average voltage across the capacitor $v_C$>0 as shown schematically in FIG. 18.

The output of capacitor 54 is connected to a low pass filter 55 which extracts the 'average effect' $\overline{U}_E$, and also used to implement the transfer function $H_E$ of the 'stimulation effect' $x_E$ given by equation (18) by adding an amplification stage 56 after the low pass filter 55.

The modulation dynamics block 33 may be implemented by a tunable lowpass filter based on a voltage-controlled amplifier (VCA), which is used to implement the variable time constant $\tau_D(t)$ of the stimulation modulation dynamic. In such case, the VCA serves as a variable-gain of the voltage-controlled lowpass filter. Alternatively, one of many alternative ways to implement a voltage-controlled filter (VCF) may be implemented.

In order to implement the variable gain $k_D(t)$ of the stimulation modulation dynamic, a classical voltage-controlled amplifier (VCA) can be used.

The modulation saturation block 34 requires a dynamic saturation function where both the lower and upper limits can be dynamically set. Thus, the modulation saturation block 34 may be implemented by a voltage clamp operational amplifier or an equivalent circuit.

The modulation algebraic block 35, when providing an exponential function, may be implemented by a voltage-controlled amplifier (VCA), or by a commercially available integrated circuit that directly offers an exponential transfer function.

In the above example, the electrophysiological signal is a beta band signal which is an example of a signal representing a frequency domain parameter. However, as an alternative, the electrophysiological signal represented by the prior signal may be the LFP signal itself, which is a voltage measured from the target area, or more generally any signal measured from the target area. This is possible, with appropriate adaption of the model implemented by the emulation apparatus 1, because the frequency domain parameter is derived in a linear manner from the measured signal. In this case, the emulation signal output from the emulation apparatus is similarly the signal measured from the target area derived under the influence of the stimulation signal. In this case, if the frequency domain parameter, for example the beta band signal, is of interest, then emulation apparatus 1 may further comprise a frequency domain processing unit (not shown) which processes the emulation signal in the frequency domain to derive a processed emulation signal representing a frequency domain parameter of the electrophysiological signal derived under the influence of the stimulation signal.

Figure 19:
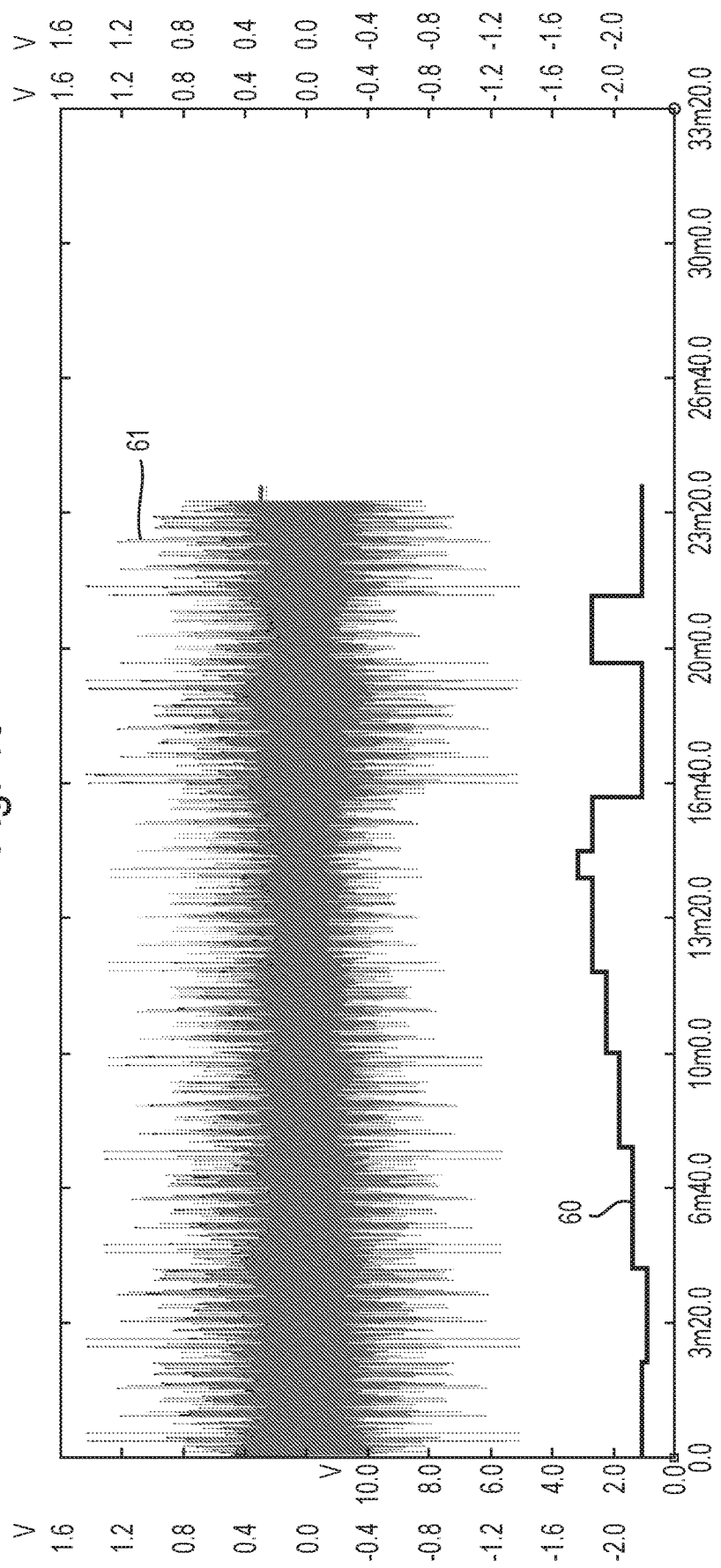
FIGS. 19 to 22 are plots of signals developed within a hardware implementation of the emulation apparatus, with different magnifications.
Figure 20:
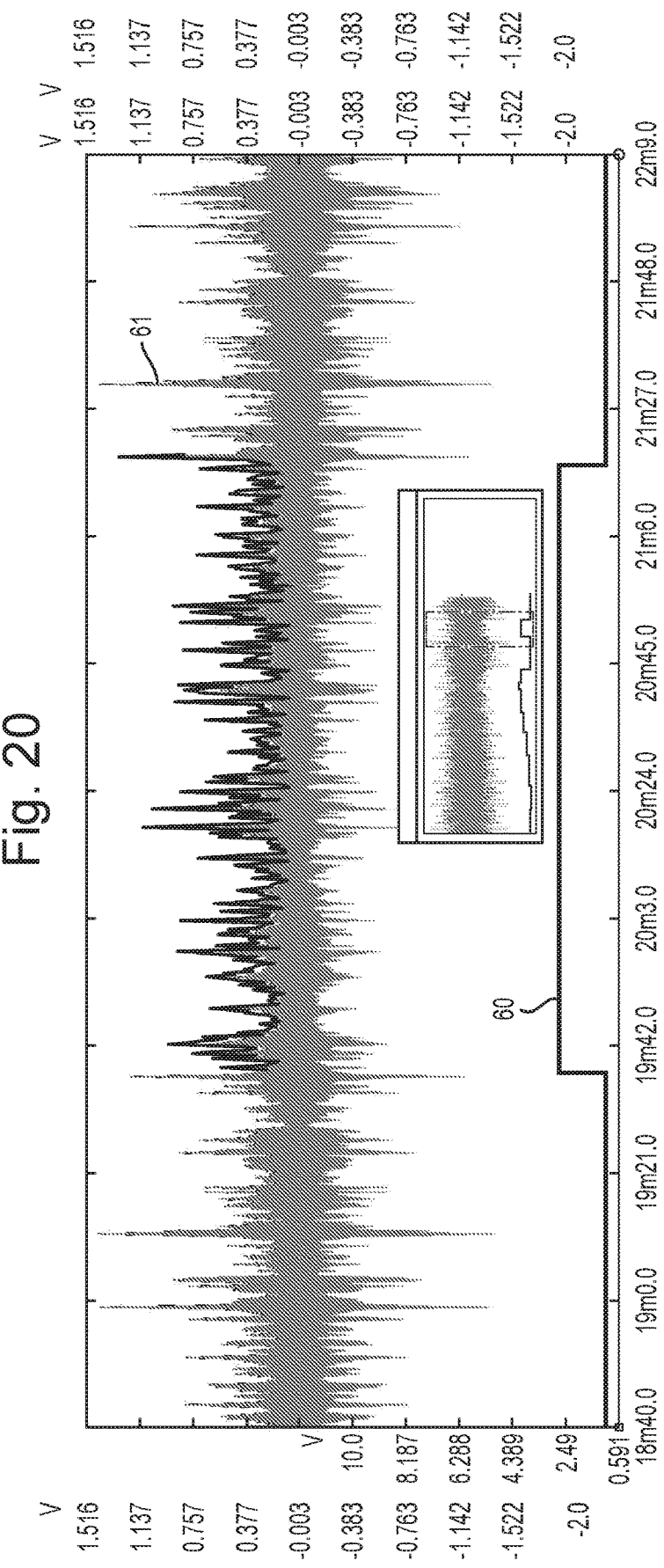
Figure 21:
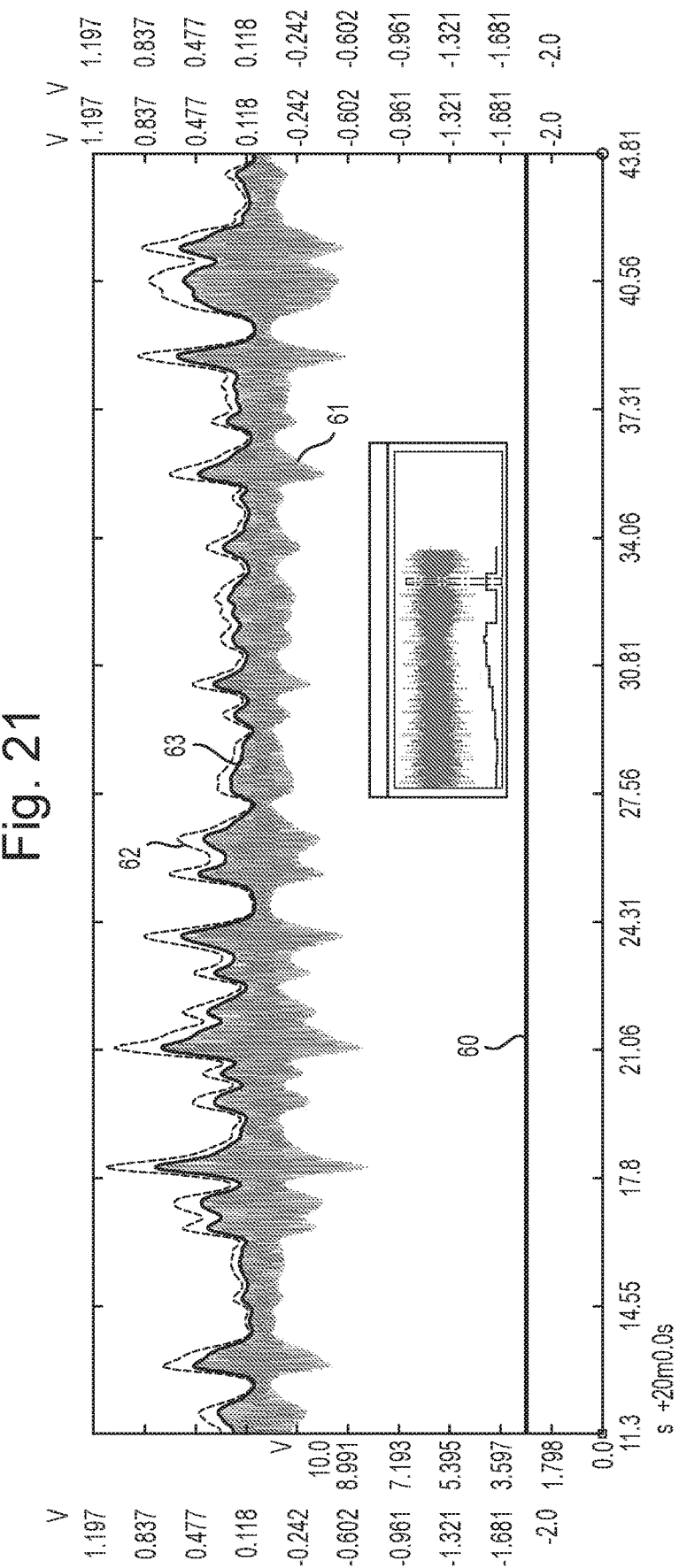
Figure 22:
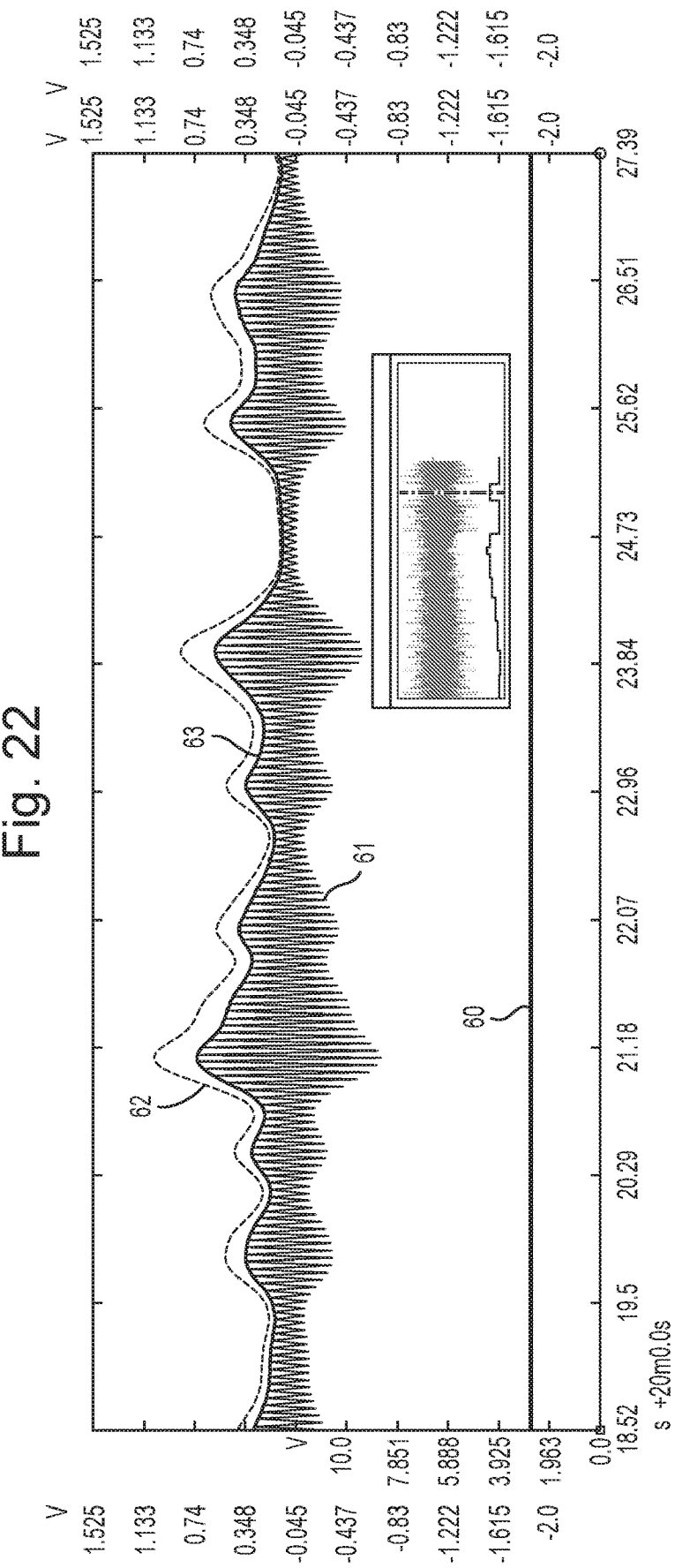

FIG. 19 shows an example of signals developed within a hardware implementation of the emulation apparatus. FIG. 20 shows the same hardware emulated signal as FIG. 19 but magnified for the time period between 18 m 40 s and 22 m 90 s. FIG. 21 shows the same hardware emulated signal as FIG. 19 but magnified for the time period between 20 m 11 s and 20 m 43 s. FIG. 22 shows the same hardware emulated signal as FIG. 19 but magnified for the time period between 20 m 18 s and 20 m 27 s. The data was recorded with a PicoScope 5442B and the PicoScope software (version 6.13.6.3775). The plots show the actual stimulation amplitude 60 and the beta power LFP estimated oscillations 61, the beta power LFP initial envelope 62 and the beta power LFP estimated envelope 63.

This example is the same as above, but this time the modulation level is determined by the hardware implementation. In particular, the modulation is derived directly from the actually generated stimulation pulses whose amplitude is directly controlled by the actual stimulation amplitude $u_a$ applied to the participant brain. The only difference is that, when the stimulator is turned OFF, the minimum amplitude $u_{a_{OFF}}$ determined by the equation below:

$$u_{a_{OFF}}(V) = -\frac{\ln\left(\frac{\rho_\infty}{\rho_0}\right)}{k_E \cdot k_D \cdot u_{P_{OFF}} \cdot u_{f_{OFF}}} \quad (54)$$

The minimum amplitude $u_{a_{OFF}}$ is necessary to guarantee that when the stimulator is turned OFF, the emulator calculates the right modulation amplitude, which the modulization has shown to be slightly higher than the actual amplitude of the beta activity recorded from the patient. For the current patient results shown here, $u_{a_{OFF}} \approx 1.055$ V.

This real-world data shows that the hardware emulator can remarkably well replicate actual electrical data recorded from actual patient brain, and therefore offers accurate patient brain activity emulation.

Figure 23:
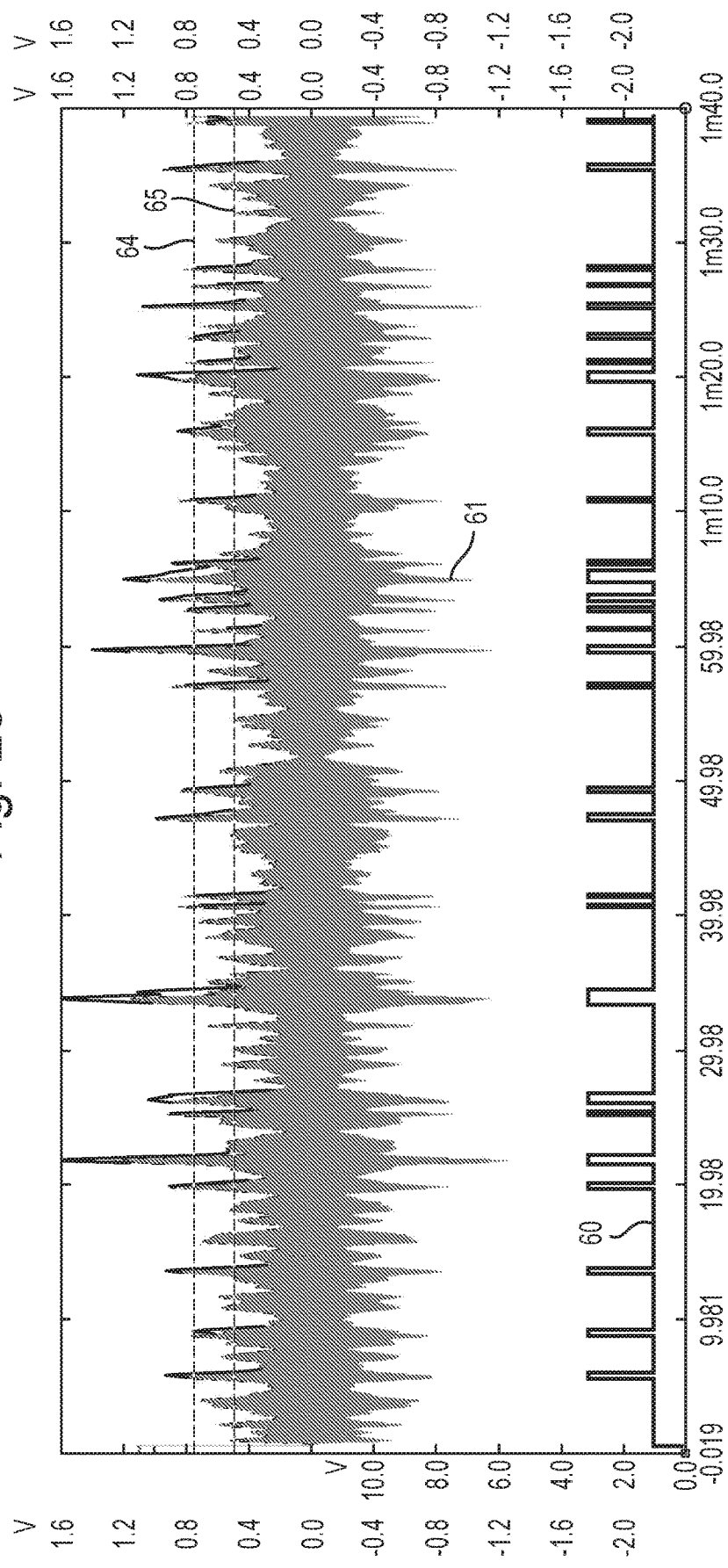
FIGS. 23 and 24 are plots of signals developed within a hardware implementation of the emulation apparatus in closed-loop, with different magnifications.
Figure 24:
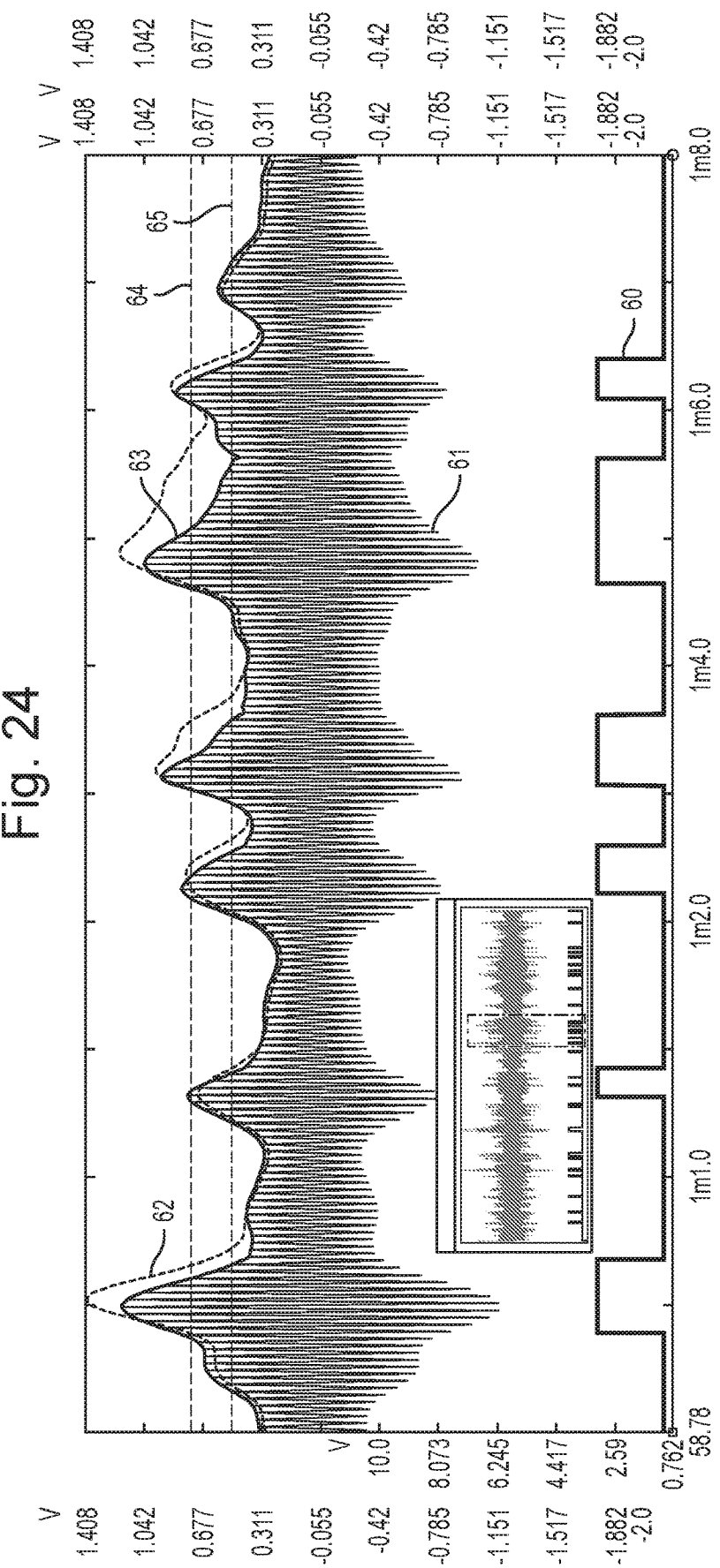

FIG. 23 shows an example of signals developed within a hardware implementation of the emulation apparatus in closed-loop. FIG. 24 shows the same hardware emulated signal as FIG. 23 but magnified for the time period between 58 s and 1 m 8 s. The plots show the actual stimulation amplitude 60 and the beta power LFP estimated oscillations 61, the beta power LFP initial envelope 62 and the beta power LFP estimated envelope 63.

This example implements the current state-of-the-art in closed-loop DBS in Parkinson's disease disclosed in [Reference 14]. Contrary to [Reference 14], in this example, we set two threshold values 64 and 65 for the beta power LFP estimated envelope 63, the higher threshold 64 being at 0.75 (representing here the classically used 75% percentile threshold value as in [Reference 1]), and the lower threshold 65 being at 0.5 (representing here therefore 50% percentile).

When the temporal beta burst activity increases above the higher threshold 64, the stimulation is turned ON with an amplitude of 3 V, pulse-width of 60 µs and at a frequency of 130 Hz as with current standard in clinical applications. Then, when the temporal beta (envelope) activity decreases below the lower threshold 65, the stimulation is turned OFF again.

This real world data shows that the emulation apparatus is able to replicate closely the switching pattern found in the literature during an aDBS control algorithm as disclosed in [Reference 14].

Overall, these open- and closed-loop results demonstrate the potential of the software and hardware emulation apparatuses to provide the state-of-the art in brain signal emulation to support the design and real-time implementation of advanced control algorithms for treating neurophysiological disorders in human.

REFERENCES

[Reference 1] Tinkhauser, G., Pogosyan, A., Little, S., Beudel, M., Herz, D. M., Tan, H., & Brown, P., (2017), «*The modulatory effect of adaptive deep brain stimulation on beta bursts in parkinson's disease*», Brain, vol. 140, no 4, p. 1053-1067, Web: https://academic.oup.com/brain/article/140/4/1053/2993763

[Reference 2] Wills, A., Schön, T. B., Ljung, L., & Ninness, B., (2013), «*Identification of hammerstein-wiener models*», Automatica, vol. 49, no 1, p. 70-81, Web: http://www.sciencedirect.com/science/article/pii/S0005109812004815

[Reference 3] Qian, X., Chen, Y., Feng, Y., Ma, B., Hao, H., & Li, L., (2017), «*A method for removal of deep brain stimulation artifact from local field potentials*», IEEE transactions on neural systems and rehabilitation engineering: a publication of the IEEE Engineering in Medicine and Biology Society, vol. 25, no 12, p. 2217-2226.

[Reference 4] Koss, A. M., Alterman, R. L., Tagliati, M., & Shils, J. L., (2005), «*Calculating total electrical energy delivered by deep brain stimulation systems*», Annals of Neurology, vol. 58, no 1, p. 168-168, Web: http://doi.wiley.com/10.1002/ana.20525

[Reference 5] Oppenheim, A. V., Willsky, A. S., & Nawab, S. H., (1997), «*Signals & systems*», 2nd ed. Upper Saddle River, N.J: Prentice Hall.

[Reference 6] Hutcheon, B. & Yarom, Y., (2000), «*Resonance, oscillation and the intrinsic frequency preferences of neurons*», Trends in Neurosciences, vol. 23, no 5, p. 216-222, Web: http://linkinghub.elsevier.com/retrieve/pii/S0166223600015472

[Reference 7] Grossman, N., Bono, D., Dedic, N., Kodandaramaiah, S. B., Rudenko, A., Suk, H.-J., . . . Boyden, E. S., (2017), «*Noninvasive deep brain stimulation via temporally interfering electric fields*», Cell, vol. 169, no 6, p. 1029-1041.e16, Web: https://linkinghub.elsevier.com/retrieve/pii/S0092867417305846

[Reference 8] Ogata, K., (2002), «*Modern control engineering edition: fourth*». New Delhi: Prentice-Hall.

[Reference 9] Birdno, M. J. & Grill, W. M., (2008), «*Mechanisms of deep brain stimulation in movement disorders as revealed by changes in stimulus frequency*», Neurotherapeutics, vol. 5, no 1, p. 14-25.

[Reference 10] van Albada, S. J. & Robinson, P. A., (2009), «*Mean-field modeling of the basal ganglia-thalamocortical system. i*», Journal of Theoretical Biology, vol. 257, no 4, p. 642-663, Web: http://linkinghub.elsevier.com/retrieve/pii/S0022519308006486

[Reference 11] van Albada, S. J., Gray, R. T., Drysdale, P. M., & Robinson, P. A., (2009), «*Mean-field modeling of the basal ganglia-thalamocortical system. ii*», Journal of Theoretical Biology, vol. 257, no 4, p. 664-688, Web: http://linkinghub.elsevier.com/retrieve/pii/S0022519308006474

[Reference 12] Grado, L. L., Johnson, M. D., & Netoff, T. I., (2018), «*Bayesian adaptive dual control of deep brain stimulation in a computational model of parkinson's disease*», PLOS Computational Biology, vol. 14, no 12, p. e1006606, Web: https://journals.plos.org/ploscompbiol/article?id=10.1371/journal.pcbi.0.1006606

[Reference 13] Sooksood, K., Stieglitz, T., & Ortmanns, M., (2010), «An active approach for charge balancing in functional electrical stimulation», IEEE Transactions on Biomedical Circuits and Systems, vol. 4, no 3, p. 162 170.

[Reference 14] Little, S., Pogosyan, A., Neal, S., Zavala, B., Zrinzo, L., Hariz, M., . . . Brown, P., (2013), 'Adaptive deep brain stimulation in advanced parkinson disease: adaptive dbs in pd', Annals of Neurology, vol. 74, no. 3, pp. 449-457, Web: http://doi.wiley.com/10.1002/ana.23951

The invention claimed is:

1. An emulation apparatus arranged to emulate an electrophysiological signal derived from a target area of the nervous system of a human or animal body under the influence of a stimulation signal applied to the human or animal body, the emulation apparatus comprising:
 a prior signal generator arranged to generate a prior signal representing the electrophysiological signal derived from the target area of the nervous system of the human or animal body in the absence of the stimulation signal;
 a test signal input arranged to receive a test signal representing the stimulation signal applied to the human or animal body;
 a modelling unit arranged to derive a modulation signal, which modulation signal represents a degree of modulation of the electrophysiological signal by the stimulation signal, from the test signal in accordance with a model implemented within the modelling unit of a temporal evolution of the modulation of the electrophysiological signal caused by the stimulation signal; and
 a modulation unit arranged to modulate the prior signal in accordance with the modulation signal to output an emulation signal representing an electrophysiological signal derived under the influence of the stimulation signal.

2. An emulation apparatus according to claim 1, wherein the model represents an algebraic change in the modulation with at least one parameter of the stimulation signal.

3. An emulation apparatus according to claim 1, wherein the model includes two cascaded differential stages with time constants of different orders of magnitude.

4. An emulation apparatus according to claim 3, wherein one of the time constants correspond to a low pass response of neural membranes of neurons to the stimulation signal.

5. An emulation apparatus according to claim 3, wherein one of the time constants represents a dynamic response of a gross average of the electrophysiological signal derived from the target area of the nervous system to the stimulation signal.

6. An emulation apparatus according to claim 1, wherein the model further represents a saturation of the modulation at a magnitude that is dependent on at least one parameter of the stimulation signal.

7. An emulation apparatus according to claim 6, wherein the model further represents the saturation of the modulation at magnitudes that are dependent on plural parameters of the stimulation signal.

8. An emulation apparatus according to claim 1, wherein the model represents a gain of the modulation with respect to plural parameters of the stimulation signal.

9. An emulation apparatus according to claim 1, further comprising an external disturbance signal generator arranged to generate an external disturbance signal representing external disturbances to the electrophysiological signal, the modulation unit being arranged to add the external disturbance signal to the emulation signal.

10. An emulation apparatus according to claim 9, wherein the external disturbances include one or more of:
   artefacts of the stimulation signal on the signal measured from the human or animal body;
   DC-drift bias;
   electrocardiogram artefacts; and
   electrical noise.

11. An emulation apparatus according to claim 1, wherein the electrophysiological signal comprises a signal representing a frequency domain parameter of a signal measured from the human or animal body.

12. An emulation apparatus according to claim 1, wherein the prior signal is a synthetic signal, or the prior signal is, or is derived from, a signal measured from an actual human or animal body.

13. An emulation apparatus according to claim 1, wherein the test signal comprises a temporal signal representing the stimulation signal or comprises parameters representing a waveform of the stimulation signal.

14. An emulation apparatus according to claim 1 implemented by electronic components.

15. A method of emulating an electrophysiological signal derived from a target area of the nervous system of a human or animal body under the influence of a stimulation signal applied to the human or animal body, the method comprising:
   generating a prior signal representing the electrophysiological signal derived from the target area of the nervous system of the human or animal body in the absence of the stimulation signal;
   receiving a test signal representing the stimulation signal applied to the human or animal body;
   deriving a modulation signal, which modulation signal represents a degree of modulation of the electrophysiological signal by the stimulation signal, from the test signal in accordance with a model of a temporal evolution of the modulation of the electrophysiological signal caused by the stimulation signal; and
   modulating the prior signal in accordance with the modulation signal to output an emulation signal representing an electrophysiological signal derived under the influence of the stimulation signal.

16. A method according to claim 15, wherein the model represents an exponential decrease in the modulation with at least one parameter of the stimulation signal.

17. A method according to claim 15, wherein the model includes two cascaded first-order continuous-time stages with time constants of different orders of magnitude.

18. A method according to claim 17, wherein one of the time constants represents a low pass response of neural membranes of neurons to the stimulation signal.

19. A method according to claim 17, wherein one of the time constants represents a dynamic response of an envelope of the electrophysiological signal derived from the target area of the nervous system to the stimulation signal.

20. A method according to claim 15, wherein the model further represents a saturation of the modulation at a magnitude that is dependent on at least one parameter of the stimulation signal.

21. A method according to claim 20, wherein the model further represents a saturation of the modulation at magnitudes that are dependent on plural parameters of the stimulation signal.

22. A method according to claim 15, wherein the model represents a gain of the modulation that is dependent on plural parameters of the stimulation signal.

23. A method according to claim 15, further comprising generating an external disturbance signal representing external disturbances to the electrophysiological signal, and adding the external disturbance signal to the emulation signal.

24. A method according to claim 23, wherein the external disturbances include one or more of:
   artefacts of the stimulation signal on the signal measured from the human or animal body;
   DC-drift bias;
   electrocardiogram artefacts; and
   electrical noise.

25. A method according to claim 15, wherein the electrophysiological signal comprises a signal representing a frequency domain parameter of a signal measured from the human or animal body.

26. A method according to claim 15, wherein the prior signal is a synthetic signal, or the prior signal is, or is derived from, a signal measured from an actual human or animal body.

27. A method according to wherein the test signal comprises a temporal signal representing the stimulation signal or comprises parameters representing a waveform of the stimulation signal.

28. A non-transitory computer program capable of execution by a computer apparatus and configured, on execution, to cause the computer apparatus to perform a method according to claim 15.

29. A non-transitory computer-readable storage medium storing a computer program according to claim 28.

* * * * *